United States Patent
Gerlach

(10) Patent No.: US 9,925,041 B2
(45) Date of Patent: Mar. 27, 2018

(54) EYE LENS HAVING A TORIC REFRACTIVE SURFACE PROFILE AND A SURFACE STRUCTURE THAT IS STEPPED IN A RADIAL DIRECTION

(71) Applicant: Carl Zeiss Meditec AG, Jena (DE)

(72) Inventor: Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 87 days.

(21) Appl. No.: 15/045,117

(22) Filed: Feb. 16, 2016

(65) Prior Publication Data

US 2016/0157997 A1 Jun. 9, 2016

Related U.S. Application Data

(63) Continuation of application No. PCT/EP2014/066695, filed on Aug. 4, 2014.

(30) Foreign Application Priority Data

Aug. 13, 2013 (DE) .................. 10 2013 216 020

(51) Int. Cl.
*A61F 2/16* (2006.01)
*G02B 3/06* (2006.01)
*G02C 7/06* (2006.01)

(52) U.S. Cl.
CPC .......... *A61F 2/1654* (2013.01); *A61F 2/1637* (2013.01); *A61F 2/1645* (2015.04); *G02B 3/06* (2013.01); *G02C 7/06* (2013.01); *G02C 2202/22* (2013.01)

(58) Field of Classification Search
CPC .... A61F 2/1654; A61F 2/1645; A61F 2/1637; A61F 2/1613; A61F 2/1618; A61F 2/1681; A61F 2/1602; A61F 2/1656; A61F 2002/1681; G02B 3/06; G02C 2202/22;
(Continued)

(56) References Cited

U.S. PATENT DOCUMENTS

| 8,292,953 B2 | 10/2012 | Weeber et al. |
| 8,465,543 B2 | 6/2013 | Fiala et al. |
| 8,522,653 B2 | 9/2013 | Hong et al. |

(Continued)

FOREIGN PATENT DOCUMENTS

WO 2012/083143 A1 6/2012

OTHER PUBLICATIONS

International Search Report dated Oct. 1, 2014 in international patent application PCT/EP2014/066695 on which the claim of priority is based.

(Continued)

*Primary Examiner* — David H Willse
*Assistant Examiner* — Tiffany Shipmon
(74) *Attorney, Agent, or Firm* — Walter Ottesen, P.A.

(57) ABSTRACT

An eye lens including an optical part, which has a first optical side and an opposite second optical side with respect to a direction of an optical principal axis (A) of the eye lens, wherein a toric refractive surface profile is formed on at least one of the two sides, wherein the eye lens has a surface structure that is stepped in a radial direction of the optical part in addition to the toric refractive surface profile, and the stepped surface structure is formed on at least one side.

16 Claims, 23 Drawing Sheets

(58) Field of Classification Search
CPC .......... G02C 2202/20; B29D 11/00269; B29D 11/00019
See application file for complete search history.

(56) References Cited

U.S. PATENT DOCUMENTS

| | | |
|---|---|---|
| 2003/0033013 A1 | 2/2003 | Callahan et al. |
| 2009/0164008 A1* | 6/2009 | Hong .................... A61F 2/1613 623/6.23 |
| 2011/0149236 A1 | 6/2011 | Weeber |
| 2012/0320335 A1* | 12/2012 | Weeber ................. A61F 2/1618 351/159.54 |
| 2015/0359625 A1 | 12/2015 | Argal et al. |

OTHER PUBLICATIONS

English translation of Office action of the Chinese Patent Office dated Nov. 30, 2016 in corresponding Chinese patent application 2014800543769.

International preliminary report on patentability dated Feb. 16, 2016 in international patent application PCT/EP2014/066695 on which the claim of priority is based.

* cited by examiner

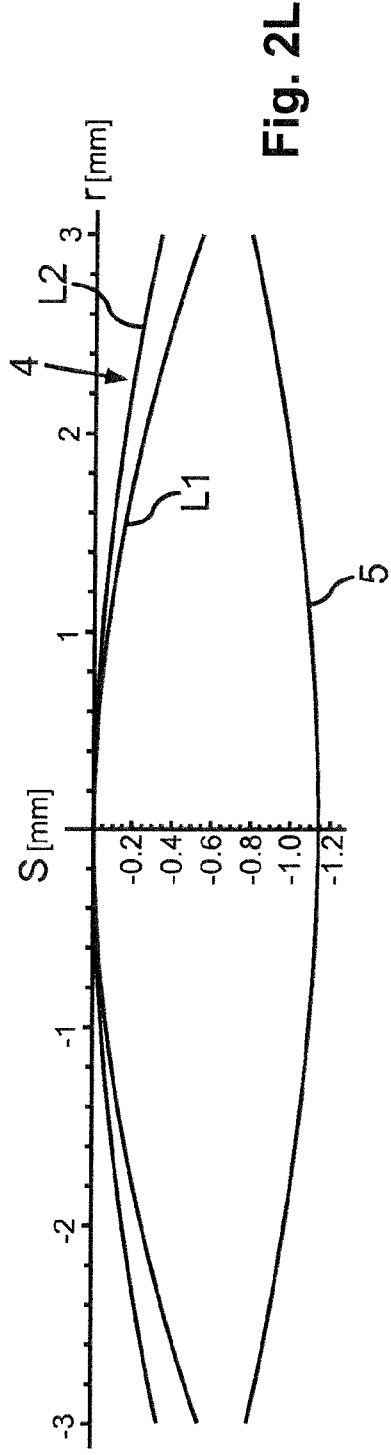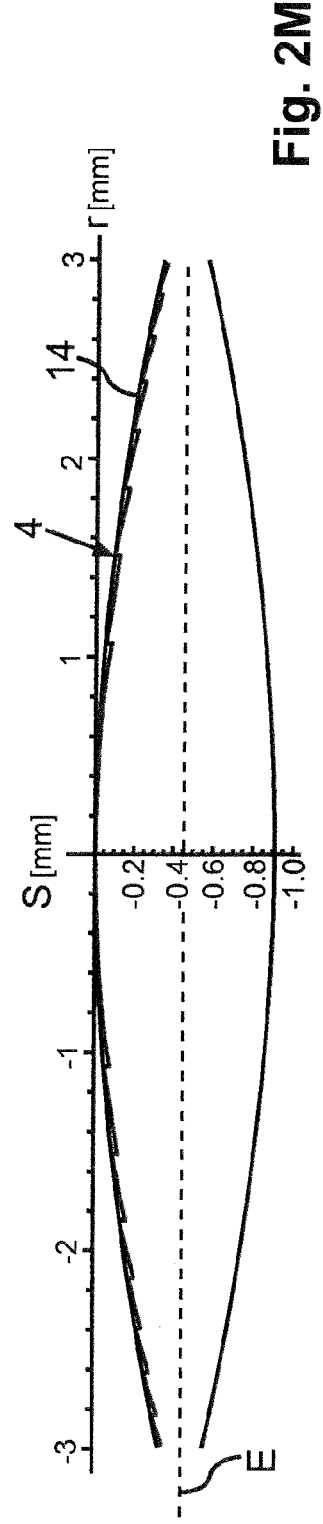

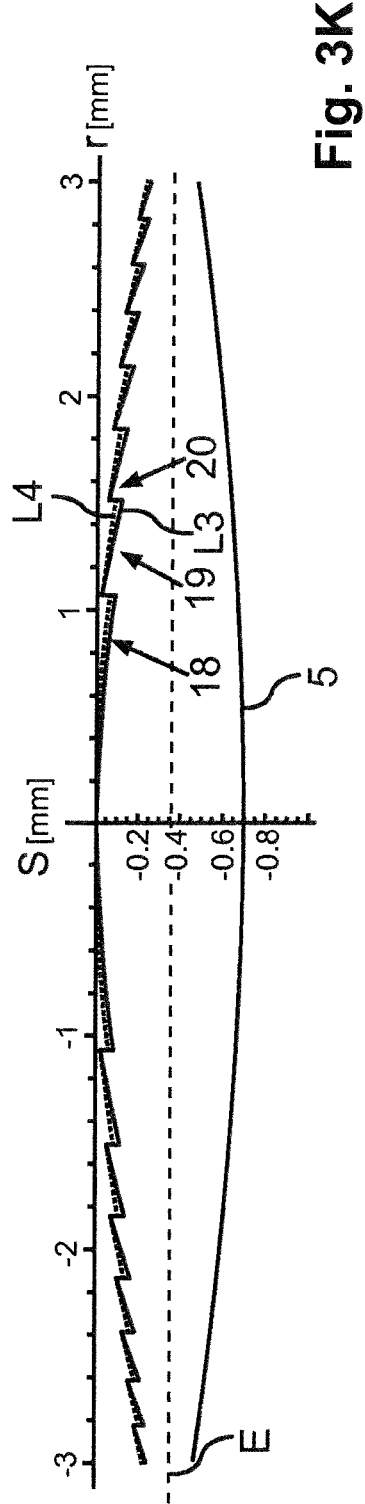

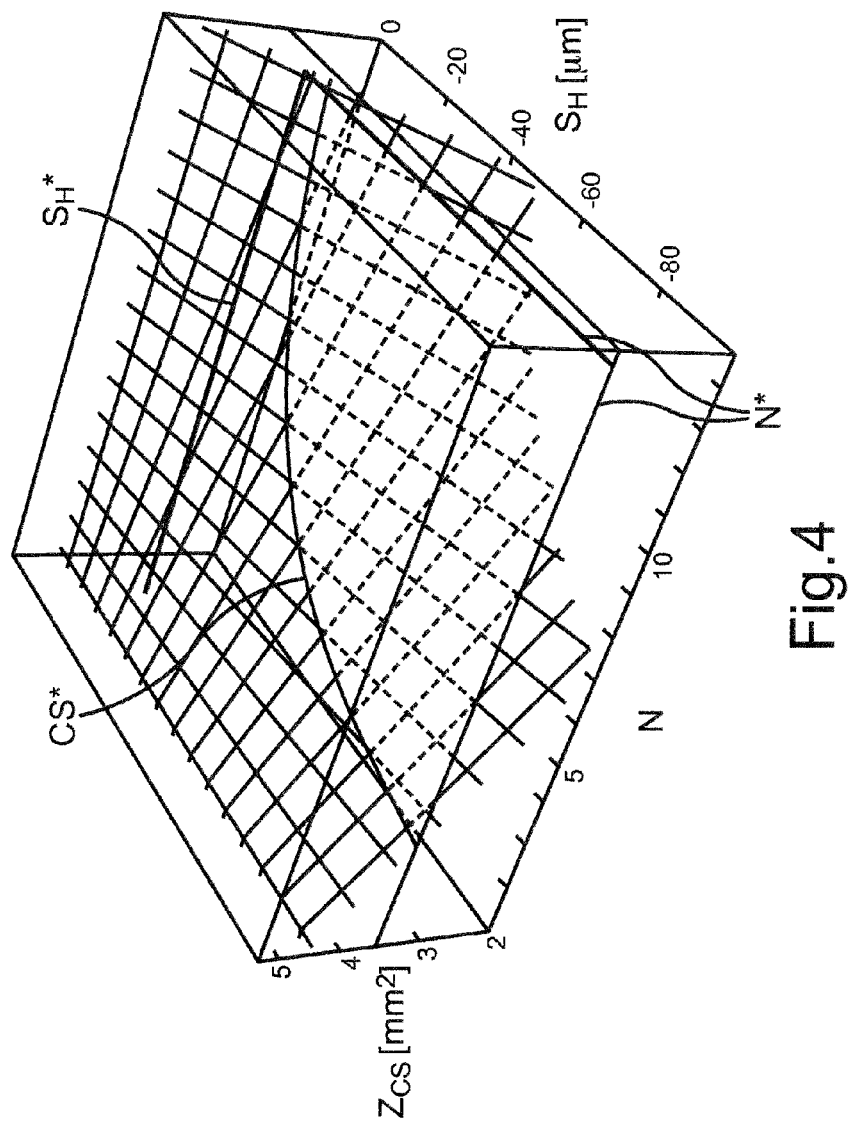

| Zone Index | rmax [mm] | r1 [mm] | r2 [mm] | K1 [mm$^{-1}$] | K2 [mm$^{-1}$] | ΔK [mm$^{-1}$] | h_Fstep @0π[μm] | h_Fstep @π/2[μm] |
|---|---|---|---|---|---|---|---|---|
| 1 | 1.13389 | 14.67 | 8.57976 | 0.0681663 | 0.116553 | 0.0483871 | 1.53814 ×10$^{-6}$ | 30.8431 |
| 2 | 1.60357 | 14.6717 | 8.58145 | 0.0681584 | 0.11653 | 0.0483719 | 2.16448 ×10$^{-6}$ | 30.3645 |
| 3 | 1.96396 | 14.6734 | 8.58315 | 0.0681505 | 0.116507 | 0.0483568 | 2.63794 ×10$^{-6}$ | 29.9723 |
| 4 | 2.26779 | 14.6751 | 8.58485 | 0.0681426 | 0.116484 | 0.0483416 | 3.03124 ×10$^{-6}$ | 29.6637 |
| 5 | 2.53546 | 14.6768 | 8.58655 | 0.0681348 | 0.116461 | 0.0483265 | 3.37273 ×10$^{-6}$ | 29.4363 |
| 6 | 2.77746 | 14.6785 | 8.58825 | 0.0681269 | 0.116438 | 0.0483113 | 3.67704 ×10$^{-6}$ | 29.2877 |
| 7 | 3. | 14.6802 | 8.58995 | 0.068119 | 0.116415 | 0.0482962 | 3.95291 ×10$^{-6}$ | 29.2156 |

Fig. 5A

| Zone Index | rmax [mm] | r1 [mm] | r2 [mm] | K1 [mm$^{-1}$] | K2 [mm$^{-1}$] | ΔK [mm$^{-1}$] | h_Fstep @0π[μm] | h_Fstep @π/2[μm] |
|---|---|---|---|---|---|---|---|---|
| 1 | 1.13389 | 9.12784 | 6.33144 | 0.109555 | 0.157942 | 0.048387 | 48.5584 | 78.7793 |
| 2 | 1.60357 | 9.12954 | 6.33314 | 0.109535 | 0.1579 | 0.048365 | 47.699 | 76.2619 |
| 3 | 1.96396 | 9.13124 | 6.33484 | 0.109514 | 0.157857 | 0.048343 | 46.8721 | 73.9283 |
| 4 | 2.26779 | 9.13294 | 6.33654 | 0.109494 | 0.157815 | 0.0483211 | 46.0757 | 71.7575 |
| 5 | 2.53546 | 9.13463 | 6.33824 | 0.109473 | 0.157773 | 0.0482991 | 45.308 | 69.7314 |
| 6 | 2.77746 | 9.13633 | 6.33994 | 0.109453 | 0.157773 | 0.0482772 | 44.5675 | 67.8348 |
| 7 | 3. | 9.13803 | 6.34763 | 0.109433 | 0.157688 | 0.0482553 | 43.8525 | 66.0547 |

Fig. 6A

| | | |
|---|---|---|
| F_Sphäre | = 20. | D |
| F_Cylinder | = 4. | D |
| CTVA | = 1 | mm |
| RoC_Face 2 | = 15.7219 | mm |
| rmax | = 3 | mm |
| nmed | = 1.336 | |
| niol | = 1.46 | |
| Number of FZones | = 7 | |
| Step Height | = 50. | μm |

| Zone Index | rmax [mm] | r1 @ 0π [mm] | r2 @ π/2 [mm] | $S_H$ [μm] |
|---|---|---|---|---|
| 1 | 1.13389 | 10.1817 | 7.65412 | 50. |
| 2 | 1.60357 | 10.186 | 7.65837 | 50. |
| 3 | 1.96396 | 10.1902 | 7.66262 | 50. |
| 4 | 2.26779 | 10.1945 | 7.66686 | 50. |
| 5 | 2.53546 | 10.1987 | 7.67111 | 50. |
| 6 | 2.77746 | 10.2029 | 7.67536 | 50. |
| 7 | 3. | 10.2072 | 7.6796 | 50. |

| Zone Index | rmax [mm] | r1 @ 0π [mm] | r2 @ π/2 [mm] | $S_H$[μm] |
|---|---|---|---|---|
| 1 | 1.13389 | 10.8221 | 6.35718 | 50. |
| 2 | 1.60357 | 10.8263 | 6.36142 | 50. |
| 3 | 1.96396 | 10.8306 | 6.36567 | 50. |
| 4 | 2.26779 | 10.8348 | 7.36992 | 50. |
| 5 | 2.53546 | 10.8391 | 6.37416 | 50. |
| 6 | 2.77746 | 10.8433 | 6.37841 | 50. |
| 7 | 3. | 10.8476 | 6.38266 | 50. |

| Zone Index | rmax [mm] | r1 [mm] | r2 [mm] | K1 [mm$^{-1}$] | K2 [mm$^{-1}$] | ΔK [mm$^{-1}$] | S$_H$[μm] |
|---|---|---|---|---|---|---|---|
| 1 | 1.13389 | 14.67 | 14.67 | 0.0681663 | 0.0681663 | 0 | -22.2789 |
| 2 | 1.60357 | 14.6717 | 14.6717 | 0.0681584 | 0.0681584 | 0 | -22.0779 |
| 3 | 1.96396 | 14.6734 | 14.6734 | 0.0681505 | 0.0681505 | 0 | -21.8817 |
| 4 | 2.26779 | 14.6751 | 14.6751 | 0.0681426 | 0.0681426 | 0 | -21.6893 |
| 5 | 2.53546 | 14.6768 | 14.6768 | 0.0681348 | 0.0681348 | 0 | -21.5004 |
| 6 | 2.77746 | 14.6785 | 14.6785 | 0.0681269 | 0.0681269 | 0 | -21.3149 |
| 7 | 3. | 14.6802 | 14.6802 | 0.068119 | 0.068119 | 0 | -21.1324 |

Fig.9

| $F_{Cyl}$ [D] | $F_{Sph}$ [D] | A_cross @ $0\pi$ [mm^2] | A_cross @ $\pi/2$ [mm^2] | N [a.u.] |
|---|---|---|---|---|
| 16. | 2. | 3.7217 | 3.93267 | 1 |
| 16. | 3. | 3.73818 | 3.05447 | 1 |
| 16. | 4. | 3.7547 | 4.17619 | 1 |
| 16. | 5. | 3.77126 | 4.29783 | 1 |
| 16. | 6. | 3.78786 | 4.4194 | 1 |
| 16. | 7. | 3.80452 | 4.54091 | 1 |
| 16. | 8. | 3.82123 | 4.66235 | 1 |
| 18. | 2. | 4.08982 | 4.29904 | 1 |
| 18. | 3. | 4.1094 | 4.42302 | 1 |
| 18. | 4. | 4.12906 | 4.54692 | 1 |
| 18. | 5. | 4.14878 | 4.67074 | 1 |
| 18. | 6. | 4.16857 | 4.7945 | 1 |
| 18. | 7. | 4.18844 | 4.91819 | 1 |
| 18. | 8. | 4.20839 | 5.04183 | 1 |
| 20. | 2. | 4.45703 | 4.66458 | 1 |
| 20. | 3. | 4.47923 | 4.79031 | 1 |
| 20. | 4. | 4.50153 | 4.91595 | 1 |
| 20. | 5. | 4.52391 | 5.04153 | 1 |
| 20. | 6. | 4.54639 | 5.16706 | 1 |
| 20. | 7. | 4.56897 | 5.29253 | 1 |
| 20. | 8. | 4.59166 | 5.41797 | 1 |
| 22. | 2. | 4.82393 | 5.02987 | 1 |
| 22. | 3. | 4.84841 | 5.15705 | 1 |
| 22. | 4. | 4.873 | 5.28416 | 1 |
| 22. | 5. | 4.8977 | 5.41123 | 1 |
| 22. | 6. | 4.64785 | 5.2646 | 2 |
| 22. | 7. | 4.67277 | 5.39176 | 2 |
| 22. | 8. | 4.49107 | 5.25356 | 3 |
| 24. | 2. | 4.65041 | 4.85552 | 3 |
| 24. | 3. | 4.67688 | 4.9843 | 3 |
| 24. | 4. | 4.70349 | 5.11305 | 3 |
| 24. | 5. | 4.73024 | 5.24178 | 3 |
| 24. | 6. | 4.75713 | 5.3705 | 3 |
| 24. | 7. | 4.78417 | 5.49919 | 3 |
| 24. | 8. | 4.54784 | 5.36589 | 4 |
| 26. | 2. | 4.75578 | 4.95991 | 4 |
| 26. | 3. | 4.78411 | 5.09007 | 4 |
| 26. | 4. | 4.81261 | 5.22022 | 4 |
| 26. | 5. | 4.84126 | 5.35034 | 4 |
| 26. | 6. | 4.87009 | 5.48044 | 4 |
| 26. | 7. | 4.63739 | 5.35025 | 5 |
| 26. | 8. | 4.66654 | 5.48034 | 5 |
| 28. | 2. | 4.86456 | 5.06784 | 5 |
| 28. | 3. | 4.89465 | 5.19931 | 5 |
| 28. | 4. | 4.92492 | 5.33075 | 5 |
| 28. | 5. | 4.95538 | 5.46212 | 5 |
| 28. | 6. | 4.72562 | 5.33431 | 6 |
| 28. | 7. | 4.75644 | 5.46553 | 6 |
| 28. | 8. | 4.52756 | 5.33834 | 7 |
| 30. | 2. | 4.71734 | 4.92026 | 7 |
| 30. | 3. | 4.74911 | 5.05313 | 7 |
| 30. | 4. | 4.78108 | 5.18588 | 7 |
| 30. | 5. | 4.81326 | 5.31841 | 7 |
| 30. | 6. | 4.84565 | 5.45055 | 7 |
| 30. | 7. | 4.61921 | 5.32479 | 8 |
| 30. | 8. | 4.65203 | 5.45572 | 8 |

EYE LENS HAVING A TORIC REFRACTIVE SURFACE PROFILE AND A SURFACE STRUCTURE THAT IS STEPPED IN A RADIAL DIRECTION

CROSS REFERENCE TO RELATED APPLICATIONS

This application is a continuation application of international patent application PCT/EP2014/066695, filed Aug. 4, 2014, designating the United States and claiming priority from German application 10 2013 216 020.8, filed Aug. 13, 2013, and the entire content of both applications is incorporated herein by reference.

FIELD OF THE INVENTION

The invention relates to an eye lens with an optical part, which has a first optical side and an opposite second optical side viewed in the direction of an optical principal axis of the eye lens. A toric refractive surface profile is formed on at least one of the two sides.

BACKGROUND OF THE INVENTION

Toric eye lenses, in particular intraocular lenses, are known from the prior art. For example, a toric intraocular lens is known from U.S. Pat. No. 8,465,543. By toric intraocular lenses, the visual defect of astigmatism is in particular corrected.

However, the known toric lenses have a relatively large volume in particular in their optical part. This is generated by the required center thickness of the optical part in the steep main meridian. Therefore, lenses with high spherical refractive power and cylinder values are only to be implanted through larger incision widths or the diameter of the optical part has to be reduced.

SUMMARY OF THE INVENTION

It is an object of the invention to provide an eye lens with a toric refractive surface profile, which is reduced in its lens volume, in particular in the optical part.

This object is, for example, achieved by an eye lens including: an optical part defining a main optical axis (A) and a radial direction; the optical part, viewed in the direction of the main optical axis (A), having a first optical side and a second optical side disposed opposite to the first optical side; a toric refractive surface profile formed on at least one of the first optical side and the second optical side; a surface structure in addition to the toric refractive surface profile; and, the surface structure being configured as a stepped surface structure stepped in the radial direction and formed on at least one of the first optical side and the second optical side.

An eye lens according to the invention includes an optical part, by which the imaging characteristics of the eye lens are characterized. This optical part has a first optical side viewed in the direction of an optical principal axis of the eye lens, which can be a front side and a rear side, and a second optical side axially opposite to the first side on the optical part, which can then be a rear side or front side depending on the first side. The optical principal axis is perpendicular to a plane of the eye lens located axially between the first and the second side, in particular the front side and the rear side, in particular of the optical part such that the sides are disposed opposite to this plane viewed along the principal axis. At least on one of the two sides and thus on at least on the front side or the rear side, a toric refractive surface profile contributing to the optical imaging characteristic of the eye lens is formed. A toric refractive surface profile is in particular characterized in that two perpendicular main meridians have different radii, in particular apex radii, and thus the curvatures, in particular apex curvatures are also different. Thereby, in particular in azimuthal direction and thus in encircling direction around the optical principal axis, a variation of the refractive power of the eye lens is achieved. By the specific configuration of the main meridians, this refractive power varies in azimuthal direction in particular corresponding to a curve course, which is formed between a start and an end at least with intermediate minima viewed in azimuthal direction.

An essential idea of the invention is to be regarded in that the eye lens has a surface structure stepped in radial direction of the optical part in addition to the toric refractive surface profile, which is formed on at least one of the two sides and which is formed at least partially encircling in particular in azimuthal direction. By such a surface structure in particular stepped in serrated manner, an optical configuration is provided, which allows that at least consistent optical imaging characteristics are involved even in toric eye lenses, but the lens volume and thus also the volume of the optical part can be substantially reduced. In particular, by this configuration with an additional serrated stepped surface structure, the extension of the optical part in axial direction is considerably reduced and thus the center thickness is also substantially reduced.

By such a configuration, thus, an eye lens is also provided, which has a substantially improved small incision capability in a configuration as an intraocular lens. This means that a considerably smaller incision in the eye is required in inserting the intraocular lens into the eye to thereby be able to introduce the intraocular lens into the eye.

The stepped surface structure is formed at least partially encircling in azimuthal direction and thus viewed around the axis.

Especially with a serrated stepped surface structure, thus, fresnelling of at least one side is in particular also formed. In particular, by fresnelling in the context of the invention, a configuration is to be understood, in which a phase deviation between two zones adjacent in radial direction and adjoining to each other and thus also a step formed therebetween is $n\lambda$, with $n>1$, in particular $\geq 10$, in particular $\geq 15$.

The visual defect of astigmatism is characterized in that the effective refractive powers of two different azimuths differ and thereby a point-shaped imaging of an object point is prevented. Usually, the two azimuths are perpendicular to each other and thereby represent main meridians. The primary source of the astigmatism of the human eye is a disturbed rotational symmetry of the human cornea. Herein, the radii of curvature differ in two perpendicular directions. Especially in the case of cataract surgery, the correction of the corneal astigmatism can be taken over by an intraocular lens and vision without glasses can be allowed to the patient.

In particular, main meridians of the toric refractive surface profile are perpendicular to each other and thus are azimuthally offset to each other corresponding to 90°.

The eye lens is in particular an intraocular lens.

Preferably, it is provided that the toric refractive surface profile and the stepped surface structure are formed and superimposed on a common side of the optical part. This can be the front side or else the rear side. By such a configuration, the position of the two different separate surface topographies can be very exactly achieved.

It can also be provided that the toric refractive surface profile is formed on a side of the optical part and the stepped surface structure is formed on the other side of the optical part. Therein, it can be provided that the toric refractive surface profile is formed on the front side and the stepped surface structure is formed on the rear side or the toric refractive surface profile is formed on the rear side and the stepped surface structure is formed on the front side. In such a configuration, the individual separate surface topographies can be very exactly produced in their contour such that the individual structures then allow very precise imaging characteristics.

It can also be provided that a toric refractive surface profile and superimposed a stepped surface structure are respectively formed both on the front side and on the rear side. The respective individual separate surface topographies are then preferably formed such that they each in sum result in the entire refractive power portion that they contribute to the overall refractive power of the eye lens. Compared to application of a surface topography only to one of the two sides, division of the optical effect with respect to the refractive power distribution is effected by this application to both sides.

In an advantageous configuration, it is provided that a radial curve course of a reference connecting curve, which intersects steps formed on one side of the optical part respectively in axial length ratio position identical in comparison of the lengths of the steps related to the individual axial lengths of these steps and thus the step heights, corresponds to a contour course of the surface of the opposite other side mirrored on a plane of symmetry of the eye lens perpendicular to the optical principal axis at least in sections. This means that the stepped surface structure has multiple steps with individual step heights viewed in radial direction, which in particular decrease with increasing radius. Due to this variation of the step heights, the reference connection curve is not respectively to be intersected by an absolute value of a length of a step height, but in a percentage length portion of the respective step. This means that for example in a first step, which has a step height a, and in a following step, which has a step height b different thereto, the reference connecting curve intersects both step heights in a percentally identical length portion. This means that the reference connecting curve then intersects the first step height for example at 50% of the step height a and the second step also at 50% of the step height b. This specific percentage value is then also taken as a basis in all of the other step heights. This means that the reference connecting curve then intersects all of the step heights at half of their lengths in this specific embodiment. It can also be provided that the reference connecting curve intersects the steps in an identical other percentage length portion value. It can vary between 0% and 100%. Thus, the reference connecting curve can also intersect the step heights at the step bottom or else at the step tip. Especially in intersecting or connecting the step tips of the individual steps, an envelope is then taken as a basis. With such a configuration, thus, it is then advantageous that a radial contour course of an envelope connecting step tips formed on one side of steps constituting the stepped surface structure corresponds to a contour course of the surface of the opposite other side mirrored on a plane of symmetry perpendicular to the optical principal axis at least in sections.

All of the indications with regard to equalities between parameters, parameter values and topography indications made before and still made below are to be regarded also as encompassed by the invention within the scope of deviations arising by measure tolerances, manufacturing tolerances and measurement tolerances. In this context, corresponding explanations relating to substantially identical indications are also to be understood thereby.

Preferably, it is provided here that the radial curve course of a reference connecting curve corresponds to a contour course of the surface of the opposite other side mirrored on a plane of the eye lens perpendicular to the optical principal axis over at least 50%, in particular at least 75%, in particular at least 80%, in particular at least 90%, in particular 100%. Thereby, an extremely high degree of symmetry is achieved. This configuration too advantageously contributes to the reduction of the lens volume with at least consistent optical imaging characteristics. An essential advantage of this configuration is to be regarded in that the folding and injection characteristics of the eye lens if it is formed as an intraocular lens are improved by this rotational symmetry.

Moreover, by the radially stepped surface structure, in particular the fresnelling, the amplitude of the surface modulation reduces, which immediately contributes to lower acceleration values of the tool, in particular of a turning tool, in producing the eye lens and thus accommodates shorter manufacturing times.

Preferably, it is provided that a radial contour course of a flat main meridian of the toric refractive surface profile is identical to a contour course of a reference connecting curve, for example an envelope, which respectively intersects steps formed on one side in axial length ratio position identical in comparison of the lengths of the steps related to the individual axial lengths of the steps, in particular connects the step tips of steps constituting the stepped surface structure in a steep main meridian of the toric refractive surface profile. This too is an advantageous implementation and allows realizing the already above mentioned advantages.

In particular, this envelope is identical to the contour course in a non-stepped flat main meridian. With such an implementation, thus, a rotational symmetry of the contour course on the side, on which the toric refractive surface profile and the stepped surface structure are formed, is in particular then also generated. However, here, the stepping is not formed completely encircling the principal axis, but equal to zero in the flat main meridians.

In particular, this rotationally symmetrical contour course is identical to the in particular also rotationally symmetrical contour course of the opposite side of the optical part, which thus is a mirroring on a plane of the optical part perpendicular to the optical axis.

In a further embodiment, it is particularly advantageous that a radial contour course of an envelope, which connects step tips of steps constituting the stepped surface structure in a flat main meridian of the toric refractive surface profile, is identical to a contour course of an envelope, which connects step tips of steps constituting the stepped surface structure in a steep main meridian of the toric refractive surface profile. Here, it can also be provided in generalization that not only the envelope is used, which connects step tips, but also a reference connecting curve is here again generally taken as a basis, which respectively intersects steps formed on one side in length ratio position axially identical in comparison of the lengths of the steps related to the individual axial lengths of the steps. The length ratio position can be again between 0% and 100% of the step heights of the individual steps here too. In this configuration, thus, the formation of steps is realized completely encircling the axis A.

Here too, an eye lens, in particular an intraocular lens, can then be configured, which has the already above mentioned advantages.

It is particularly preferred that the mentioned radial contour courses are formed rotationally symmetrical around the principal axis and thus azimuthally encircling the principal axis.

In a further advantageous configuration, it is provided that step tips of steps constituting the stepped surface structure in a flat main meridian of the toric refractive surface profile are formed radially in the same position as step tips of steps constituting the stepped surface structure in a steep main meridian of the toric refractive surface profile. This means that the step tips each have the same radius at least in the main meridians, which are in particular perpendicular to each other. In such a configuration, the optical effect of the toric refractive surface profile is then preferably achieved by a different configuration of the step heights of the individual steps in these two different main meridians. Thus, a superposition is generated, in which steps raised to the top on the toric refractive surface profile, in particular serrated steps, are virtually generated, which are formed radially in the main meridians in the same radial position, but are differently configured with regard to their step heights.

Preferably, it is provided that step heights of steps constituting the stepped surface structure in a flat main meridian of the toric refractive surface profile are different, in particular lower, than step heights of steps constituting the stepped surface structure in a steep main meridian of the toric refractive surface profile.

Preferably, it is provided that step heights of steps constituting the stepped surface structure of the toric refractive surface profile are equal to zero only in a main meridian, in particular the flat main meridian. Very specific surface topographies for eye lenses can be generated therefrom, which then again allow individual optical imaging characteristics for correcting visual defects.

Preferably, it is provided that the first side of the optical part and the second side of the optical part are each convexly formed.

In an alternative implementation, it is provided that the first side of the optical part and the second side of the optical part are each concavely formed. In such a configuration, the center thickness of the optical part is then again substantially reduced. The foldability and small incision capability are then increased.

Preferably, it is provided that a spherical refractive power portion of the overall refractive power of the eye lens is each equally distributed to the first side and the second side. However, it can also be provided that a spherical refractive power portion of the overall refractive power of the eye lens is distributed to one side at 25% to 35% and to the other side at the rest.

The steps of the surface structure are constituted by radially adjoining annular zones encircling the optical principal axis in encircling direction, which are formed offset to each other with their surfaces. In a preferred implementation of the eye lens, the number of the zones is between 5 and 14, in particular between 7 and 14, in particular 9 or 10. Preferably, an area of a zone is between 2.7 and 3.9 mm$^2$, in particular between 2.7 and 3.1 mm$^2$ or between 3.3 and 3.6 mm$^2$. The step height is in particular between 20 μm and 80 μm.

In an advantageous implementation, it is provided that a radial course of the overall refractive power is formed with a discrete step profile having minima and the steps of the stepped surface structure are formed at the refractive power steps radially viewed. In particular, this thus means that a step tip of a step is also formed at jump locations, at which the overall refractive power changes upwards or downwards in jump-like manner.

In a further advantageous configuration, it is provided that the step heights of the steps decrease with increasing radius.

In particular, it is provided that a difference value between step heights at a steep main meridian of the toric refractive surface profile and step heights at the flat main meridian of the toric refractive surface profile of the steps decreases with increasing radius. Thus, a difference value of a step and thus also a zone located further inwards is larger than a difference value of a zone or step located radially further outwards.

Generally, the azimuth-dependent overall refractive power of an eye lens according to the invention can be represented by the following formula:

$$F_{ges}(\varphi,\rho)=F_{Sphäre}(\rho)+F_{Cylinder}(\varphi,\rho)+F_{HOA}(\varphi,\rho)+F_{EDoF}(\varphi,\rho) \quad (1)$$

with
φ=azimuthal angle
ρ=radial position on the optical part
$F_{ges}$=azimuth-dependent overall refractive power
$F_{Sphäre}$=spherical refractive power
$F_{Cylinder}$=azimuth-dependent cylindrical refractive power portion
$F_{HOA}$=azimuth-dependent refractive power portion for correcting higher order aberrations (for example, coma, five-foil error et cetera)
$F_{EDoF}$=azimuth-dependent refractive power portion for influencing the depth of focus The overall refractive power can be divided to both sides of the optical part in very different ratios for example to reduce the step heights and the local curvatures. In an advantageous configuration, an equal distribution to both sides is performed.

Moreover, a sagittal height S of the topography in an azimuth on a side of the optical part becomes determinable by the formula 2 mentioned below:

$$s(r, r_0, Q) = \frac{r^2}{r_0 \left(1 + \sqrt{1-(1+Q)\frac{r^2}{r_0^2}}\right)} \quad (2)$$

r=radial position on lens surface
$r_0$=central radius of curvature ($r_0 \to r_{target}$=radius of curvature of the target function (enveloping surface))
Q or k=conic constant An equation for determining the azimuthal apex radius of curvature describes the radial course of a conic asphere. It can be generalized by addition of polynomial coefficients or be replaced with other types of description, for example by Zernike series, polynomials, splines or Bezier curves or piecewise defined functions. By the variation of the asphericity, for example by variation of the conic constant (k), the azimuth-dependent radial refractive power course can be influenced. Advantageously, this is effected to compensate for imaging errors by spherical aberration. The value for the sagittal height determined in the above mentioned formula and thus the height viewed in the direction of the axis A can be calculated at any location of the surface of a side of the optical part. The calculation of this sagittal height in each azimuth then directly results in the three-dimensional topography of the side surface and thus in the representation of the data for a manufacturing process. In particular, the small incision capability is achieved by reduction of the lens volume by means of fresnelling depending on geometry. Therein, in the fresnelling, it is provided that the defocus increasing with increasing radial coordinate is compensated for by the displacement of the curvature centers in the respective zones, in particular Fresnel zones, by adaptation of the refractive powers in the respective Fresnel zones. The topography-dependent fresnelling allows advantageously optimizing the enveloping topography of the optical part with respect to symmetry and injection characteristics. By a suitable azimuthal variation of the step height and thus also a Fresnel tooth depth, an advantageous rotational symmetry of the envelope in this contour can be achieved. Such geometries substantially facilitate the injectivity of the eye lens formed as an intraocular lens through small incisions in the eye.

In an equal distribution of the sphere and the fresnelling of the steep main meridian corresponding to the flat main meridian, a configuration results even with high cylinder values of the eye lens, which has a rotationally symmetrical enveloping shape and is symmetrical with respect to the curvature course and the center thickness to the eye lens equator and thus to a plane of symmetry or principal plane.

The azimuth-dependent cylindrical refractive power indicated in the above mentioned formula can also be very small and preferably <0.01 diopters. However, it is preferably larger.

It is also possible that the surface topography of one of the two sides, on which for example a stepped surface structure and a toric refractive surface profile then are not formed, is adapted to the anatomic conditions of the capsular bag independently of the refractive power of the eye lens, into which the intraocular lens is inserted. The eye lens can also be a multifocal lens and can be a diffraction lens in this context. It can include a plurality of zones at least partly annularly encircling the optical axis, formed adjoining to each other in radial direction, which in particular each have at least one main sub-zone and one phase sub-zone. By means of such a sub-zone configuration of an overall zone, configurations are achieved, in which undesired interference characteristics can be compensated for, which is in particular achieved by the phase sub-zone.

The specific values of parameters and indications to ratios of parameters or parameter values specified in the documents for defining embodiments of the eye lens are to be considered as encompassed by the scope of the invention even within the scope of deviations, for example due to measurement errors, system errors, DIN tolerances et cetera, whereby explanations relating to substantially corresponding values and indications are also to be understood thereby.

BRIEF DESCRIPTION OF THE DRAWINGS

The invention will now be described with reference to the drawings wherein:

FIG. 2L is a representation of the course of a rear side as well as a front side of the intraocular lens known from the prior art in a diagram, in which the sagittal height is represented depending on the radius;

FIG. 2M is a representation of the course of a rear side and a front side of the embodiment of the eye lens according to the invention, as it is illustrated in the above mentioned diagrams, in a diagram, in which the sagittal height is shown depending on the radius;

FIG. 3K is a diagram, in which the sagittal height is represented depending on the radius for a rear side and a front side of the optical part of the exemplary eye lens according to the invention, as it is shown in FIGS. 3A to 3D and FIG. 3F as well as FIGS. 3H and 3I;

FIG. 4 is a diagram, in which a relation between a number of the annular optical zones generating a radially stepped surface structure, an area size and the step height is shown;

FIG. 5A is a table, in which values for the maximum radius, the radius at a flat main meridian and at a steep main meridian as well as the curvature in the flat and the steep main meridian, the curvature difference, the step height in the flat and the steep main meridian, the step height for an exemplary number of zones of an eye lens are represented;

FIG. 6A is a table, in which values for the maximum radius, the radius at a flat main meridian and at a steep main meridian as well as the curvature in the flat and the steep main meridian, the curvature difference, the step height in the flat and in the steep main meridian, the step height for an exemplary number of zones of an eye lens are represented;

FIG. 9 is a table, in which values for the maximum radius, the radius at a flat main meridian and at a steep main meridian as well as a curvature in the flat and the steep main meridian, the curvature difference, the step height in the steep main meridian are represented for an exemplary number of zones of an eye lens;

DESCRIPTION OF THE PREFERRED EMBODIMENTS OF THE INVENTION

Figure 1A:
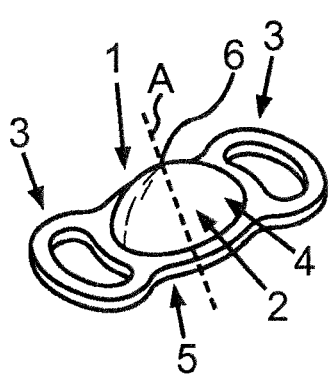
FIG. 1A is a perspective representation of a first embodiment of an eye lens according to the invention.

In the figures, identical and functionally identical elements are provided with the same reference characters.

In FIG. 1A, a first embodiment of an eye lens 1 is shown in a perspective representation, which is an intraocular lens. The eye lens 1 includes an optical part 2 and a haptic 3 adjoining thereto. The eye lens 1 is foldable and can be introduced into the eye via a small incision. The optical part 2, which is essential to the optical imaging characteristic of the eye lens 1, includes an optical principal axis A. The optical part 2 moreover has a first optical face or side 4, which can be a front side, and opposite a second optical face or side 5, which can be a rear side, viewed in the direction of this optical principal axis A. The exemplary front side 4 faces the cornea in the implanted state of the eye lens 1 in the eye, whereas the rear side faces away from this cornea.

Figure 1B:
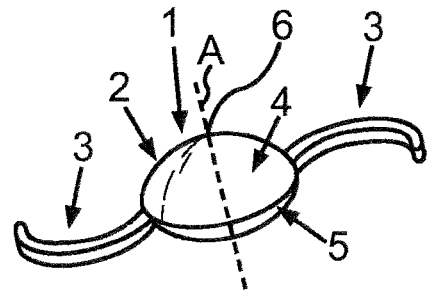
FIG. 1B is a perspective representation of a further embodiment of an eye lens according to the invention.

In FIG. 1B, a further embodiment of an eye lens 1 formed as an intraocular lens is shown in a perspective representation. It differs from the implementation in FIG. 1A by the different haptic 3. The eye lens 1 is retained in the eye by means of the haptic 3.

Basically, otherwise formed and configured haptics 3 can also be provided.

The eye lenses 1 according to FIGS. 1A and 1B have apexes 6 in their optical parts 2 on the one side 4 and the opposite side 5.

Figure 2A:
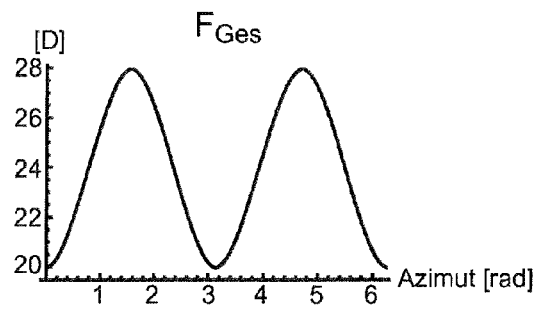
FIGS. 2A to 2D are a representation of courses of the overall refractive power, the cylindrical refractive power and the spherical refractive power as well as of the radius depending on the azimuth for an embodiment of an eye lens according to the invention.

In FIG. 2A, a diagram is shown, in which the overall refractive power $F_{Ges}$ of an embodiment of an eye lens 1 according to the invention is shown depending on the azimuth in a complete turn around the axis A. The wave-shaped course with minima and maxima is apparent, wherein the overall refractive power azimuthally varies between the values of 20 diopters and 28 diopters thereto.

Figure 2B:
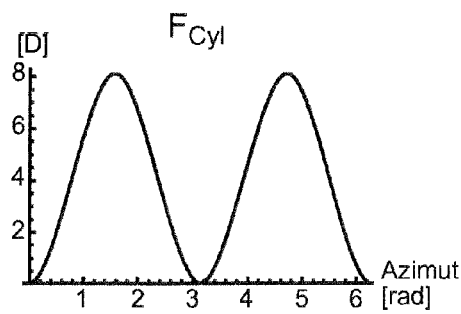

In FIG. 2B, a diagram is shown, in which the course of the azimuthal cylindrical refractive power, which is contributed to the overall refractive power by a toric refractive surface profile, is illustrated. Here, this cylindrical refractive power $F_{Cyl}$ varies between 0 and 8 diopters.

Figure 2C:
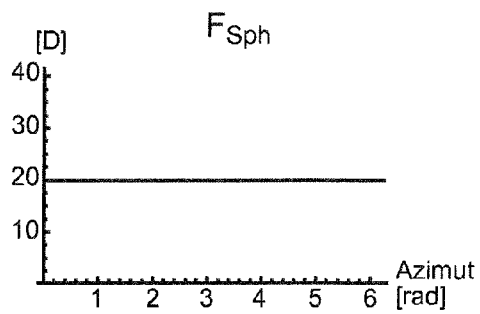

Moreover, in FIG. 2C, a diagram is shown, in which the spherical refractive power $F_{Sphäre}$ is represented depending on the azimuth in a complete turn around the axis A. It is constant in the embodiment and exemplarily has the value of 20.

Figure 2D:
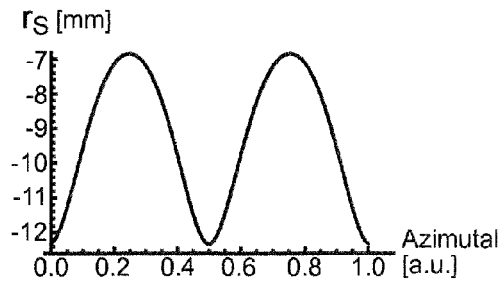

Moreover, in the diagram according to FIG. 2D, the radius, in particular the apex radius, is represented depending on the azimuthal angle, which here is not indicated in the unit [Rad] compared to the diagrams according to FIGS. 2A to 2C, but is represented in normalized form. The wave-shaped variation of this radius $r_S$ is shown.

Both the course of the cylindrical refractive power and the value of the spherical refractive power and the course of the radius of curvature are exemplary.

Figures 2E, 2F:
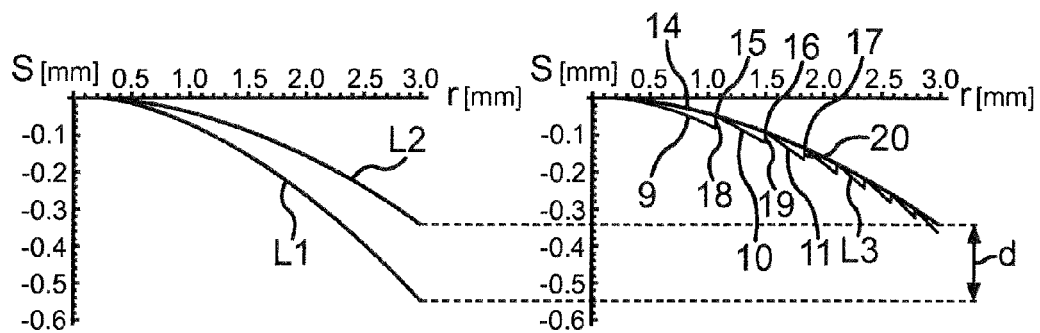
FIG. 2E is a diagram, in which the sagittal height of a toric intraocular lens according to the prior art is presented in two perpendicular main meridians.
FIG. 2F is a diagram, in which the sagittal height of the embodiment according to FIGS. 2A to 2D is shown.

In FIG. 2E, a diagram is shown, in which the sagittal height S is represented depending on the radius (r) of the optical part 2 in a toric intraocular lens from the prior art. In this context, the curve L1 shows the course at the steep main meridian, whereas the curve L2 shows the course at the flat main meridian offset by 90° thereto.

Compared thereto, in FIG. 2F, a diagram is shown, in which the sagittal height is shown depending on the radius of the embodiment of an eye lens 1 according to the invention. In this context, it is to be mentioned that a side 4 or a side 5 or both sides 4 and 5 are correspondingly configured with a surface topography, which has a toric refractive surface profile 7 (FIG. 2K) and a surface structure 8 serrated stepped in radial direction of the optical part 2 in addition to the toric refractive surface profile 7, wherein the serrated stepped surface structure 8 is also formed on at least one side (4, 5).

Figure 2G:
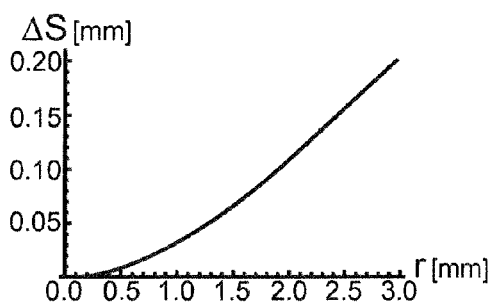
FIG. 2G is a diagram, in which the sagittal height difference between the two main meridians, as it is represented in FIG. 2E, is shown.
Figure 2H:
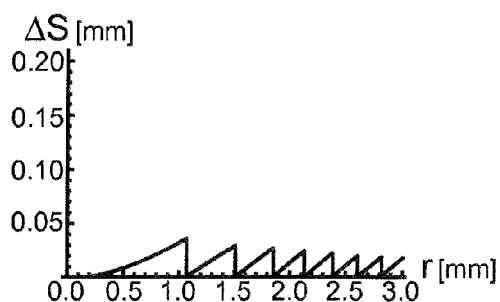
FIG. 2H is a diagram, in which the sagittal height difference of the embodiment of the eye lens according to the invention in FIG. 2F is shown.
Figure 2I:
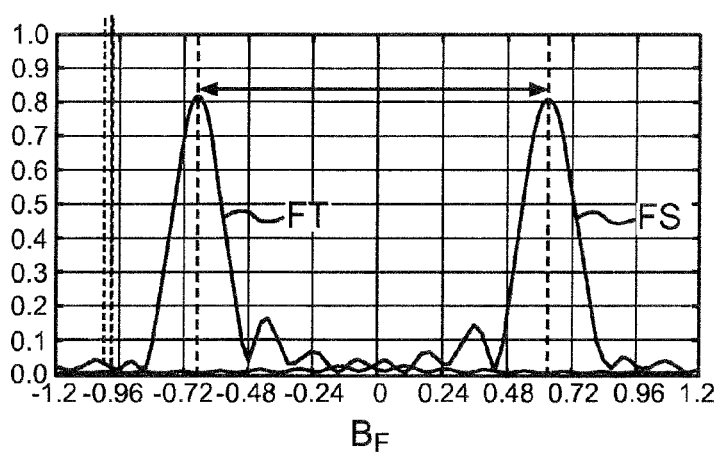
FIG. 2I is a diagram, in which the widths of the tangential focus and the sagittal focus of the embodiment of the eye lens according to the invention are shown.
Figure 2J:
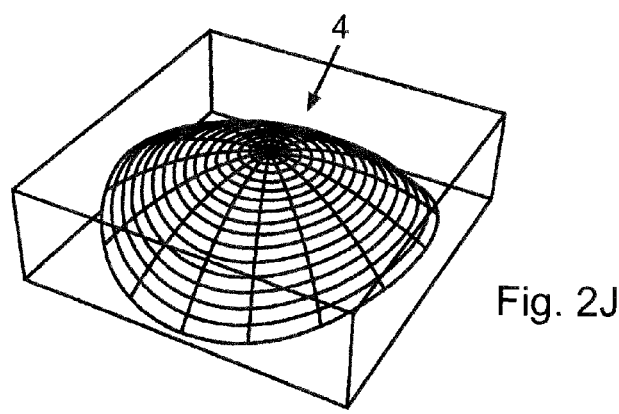
FIG. 2J is a three-dimensional representation of a surface topography of the intraocular lens known from the prior art according to the diagrams in FIGS. 2E and 2G.
Figure 2K:
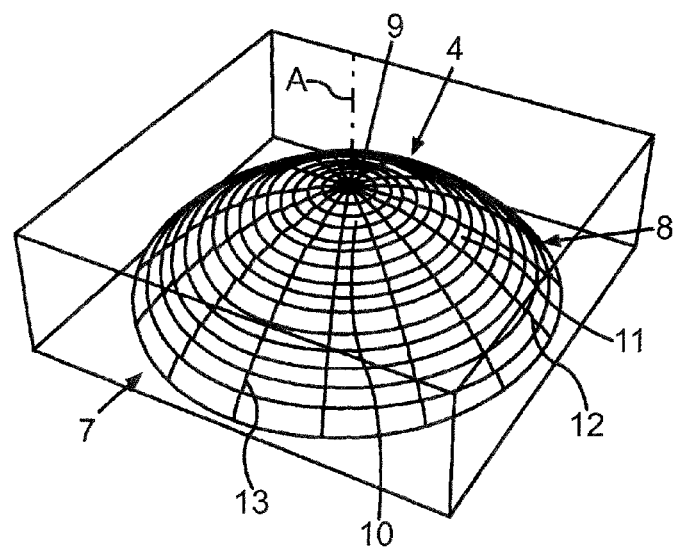
FIG. 2K is a representation of a three-dimensional surface topography of a side of an optical part of the embodiment of the eye lens according to the invention, as it is shown in FIGS. 2A to 2D and FIGS. 2F and 2H as well as 2I.

In the embodiment according to FIG. 2K, in which a surface topography of the embodiment is three-dimensionally represented, the toric refractive surface profile 7 and the radially serrated stepped surface structure 8 are formed superimposed on one side, for example the side 4.

In the embodiment, it is provided that the stepped surface structure 8 is a fresnelling and includes a plurality of annularly encircling zones (9, 10, 11), wherein it is to be mentioned here that only some of the annular zones directly adjoining to each other in radial direction are provided with a corresponding reference character for the sake of clarity. These zones 9 to 11, of which the innermost zone 9 representing a circular area is also referred to as annular zone, adjoin to adjacent zones at their radial inner and outer boundaries, wherein a step is respectively formed between two zones. This means that the adjoining edges of the adjacent zones are formed offset to each other in the direction of the axis A by a step height in particular oriented in axial direction.

In the representation in FIG. 2F, a curve L3 is shown, which shows the stepped course of the corresponding steps between the zones 9 to 11 on the side 4 at a steep main meridian 13 having a smaller radius compared to a flat main meridian 12 of the toric refractive surface profile 7.

Moreover, it is apparent that a radial contour course of an envelope 14, which connects the step tips 15, 16 and 17 formed on one side 4 of steps 9 to 11 constituting the stepped surface structure 8, corresponds at least in sections, in particular completely, to a contour course of the surface of the opposite other side 5 mirrored on a geometry plane E (FIG. 2M) of the optical part 2 of the eye lens 1 perpendicular to the optical principal axis A. This means that according to the representation in FIG. 2M, in which the sagittal height S is represented depending on the radius (r) of the embodiment of the eye lens 1 according to the invention, represents the side 5, in particular a rear side, which corresponds to the envelope 14 mirrored on the plane E, which connects the step tips 15 to 17, which are provided with a reference character representative for all of the other step tips of the further steps.

In the embodiment according to FIG. 2F, it is also provided that the radial contour course of a flat main meridian 12 of the toric refractive surface profile is identical to the contour course of the envelope 14. In particular, the contour course of the side 4 is rotationally symmetric around the axis A.

However, instead of the envelope 14, another reference connecting curve can also be taken as a basis, which for example does not connect the step tips, but the step bottoms of the zones 9 to 11. Similarly, a reference connecting curve can be taken as a basis, which each depending on a percentage length ratio and thus on an axial length ratio position of each individual step height of steps 18, 19 and 20, which are again provided with reference characters representative for all of the other steps, intersects them. Thus, it can be provided that the reference connecting curve each intersects all of the steps in their step height at 50% of the entire step height, respectively.

By these advantageous implementations realizable both individually and in combination, the specific radial serrated stepping, the configuration of the steps 18 to 20 and/or the step tips 15 to 17 such that they are on a reference connecting curve, which is mirror symmetrical to an opposite side 5 of the optical part and/or in which the flat meridian 5 corresponds to the envelope 14 connecting the step tips 15 to 17, in course, a substantial reduction of the volume of the optical part 2 can be achieved. In FIGS. 2E and 2F, it is exemplarily shown, how much reduction of the center thickness of the optical part 2 can be achieved, which is indicated by the thickness d in FIG. 2F, which is exemplarily between 0.15 and 0.25, in particular substantially 0.2 mm.

In FIG. 2G, the difference of the sagittal height or the sagittal height difference $\Delta S$ is shown depending on the radius of the two curves L1 and L2 in FIG. 2E in a diagram. Thus, a course is shown, as it occurs in lenses from the prior art. It is apparent that this sagittal height distance increases, in particular greatly increases, with increasing radius ?r.

In contrast, in FIG. 2H, this sagittal height difference ?S is shown for an embodiment of the invention, as it was explained with respect to FIG. 2F. Here, it is apparent that this sagittal height difference $\Delta S$ becomes smaller with increasing radius. In particular, in this context, it is advantageous if a difference value between the step height at the steep main meridian 13 and the step height at the flat main meridian 12 of the steps decreases with increasing radius (r). In the representation in FIG. 2A, it is apparent that the maximum sagittal height difference is at about 0.035 mm and then radially decreases.

In FIG. 2I, a diagram is shown, in which the widths $B_F$ of a tangential focus FT and a sagittal focus FS are represented. Here, an astigmatism of about 6 diopters is taken as a basis, which corresponds to the distance of the maxima of the tangential focus and the sagittal focus.

In FIG. 2J, compared to the representation in FIG. 2K, a three-dimensional representation of a surface topography of a side of the optical part of a toric intraocular lens known from the prior art is shown. The different radii are clearly recognizable in this context.

In contrast, in FIG. 2K, a constant radius is formed in all of the zones in azimuthal direction, and the superposition of the toric refractive surface profile 7 with the serrated stepped surface structure 8 is achieved to the effect that the step heights vary in azimuthal direction and are maximally different in particular at the meridians 12 and 13.

In FIG. 2L, a diagram is shown, in which the sagittal height S is shown depending on the radius (r) for the known lens according to FIG. 2J. Here too, the side 5 is shown, wherein the side 4 is shown with the flatter course L2 in the flatter main meridian and L1 in the steeper main meridian. A symmetrical configuration to a plane E is completely improbable in FIG. 2L.

Moreover, by the comparisons of FIG. 2L and an embodiment of an eye lens according to the invention according to FIG. 2M, the reduction of the center thickness also again becomes clear. The rotationally symmetrical configuration of the envelope 14 is also apparent, which thus also illustrates a rotationally symmetrical configuration of the serrated stepped surface structure 7.

Figure 3A:
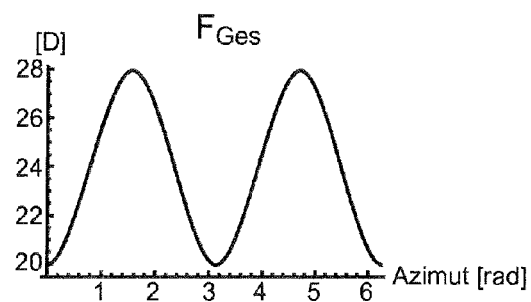
FIGS. 3A to 3D are a representation of diagrams, in which the overall refractive power, the cylindrical refractive power and the spherical refractive power of a further embodiment of an eye lens according to the invention as well as the course of the radius of the lens are shown depending on the azimuth.

In FIG. 3A, a diagram is shown, in which the overall refractive power $F_{Ges}$ is shown depending on the azimuth for a complete turn around the axis A for a further embodiment of an eye lens 1 according to the invention.

Figure 3B:
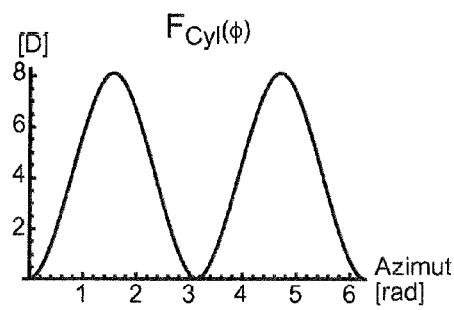
Figure 3C:
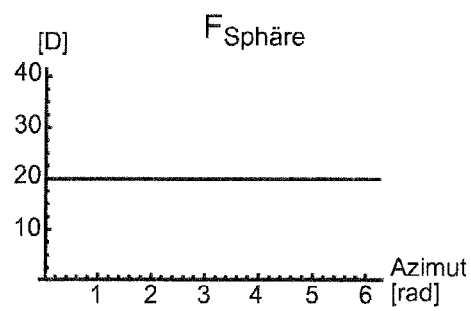
Figure 3D:
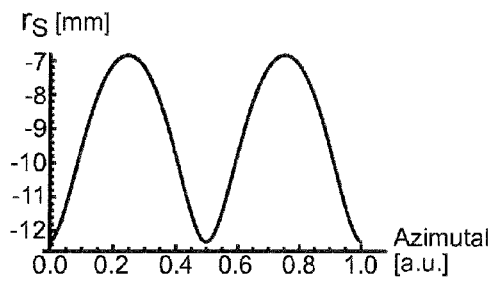

Moreover, in FIG. 3B, a diagram is shown, in which the cylindrical refractive power $F_{Cyl}$ is shown depending on the azimuth. Thereby, the portion of the toric refractive surface profile 7 of the overall refractive power is also illustrated. Moreover, a diagram is shown in FIG. 3C, in which the spherical refractive power $F_{Sphäre}$ is represented depending on the azimuth and exemplarily is constant, in particular has the value of 0.

In the diagram according to FIG. 3B, the radius, in particular the apex radius $r_S$, is again shown depending on the normalized azimuth angle.

In the embodiment in FIGS. 2A to 2M, it is provided that refractive powers of the sphere are distributed to the side 4 and the side 5 of the eye lens 1 in equal shares. Despite the high cylindrical value, an eye lens results therefrom, which has a rotationally symmetrical envelope 14 and moreover is symmetrical with respect to the curvature course and the center thickness to the lens equator and thus to the plane E. By the specific fresnelling, the envelope 14 of the steep meridian 13 is exactly adapted to the flat meridian 12, as it is shown in FIGS. 2F and 2M.

In the embodiment in FIG. 3A ff., it is in particular provided that the distribution of the refractive powers to the side 4 and to the side 5 is not equal, but that for example refractive powers of the sphere are distributed at 25% to 35% to a side 4 or 5 and the remaining portion to the other side 5 or 4. Thereby, it is allowed increasing the radius of curvature of the side having the smaller refractive power portion by at least 80%, in particular 90%. For example, it can be provided that the distribution of the refractive powers of the sphere is 6.2 diopters on the front side and 13.8 diopters on the rear side, if the overall spherical refractive power is 20 diopters as it is illustrated in FIG. 3C.

Figures 3E, 3F:
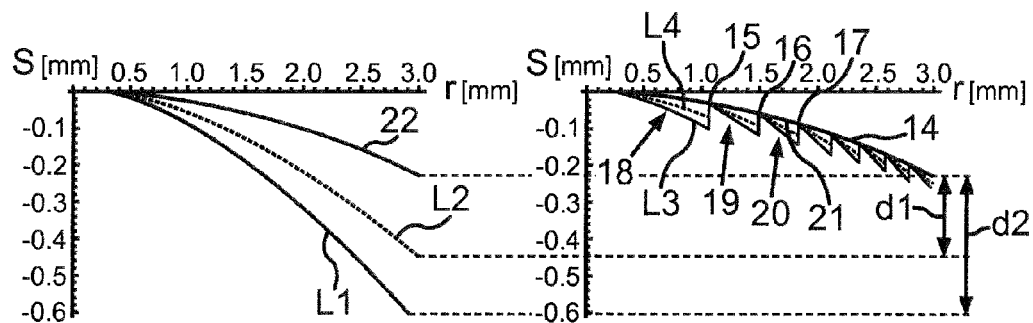
FIG. 3E is a diagram, in which the sagittal height is represented at two perpendicular main meridians depending on the radius of an eye lens known from the prior art.
FIG. 3F is a representation of a diagram, in which the sagittal height is shown depending on the radius for the embodiment of an eye lens according to the invention according to FIGS. 3A to 3D at two different, perpendicular main meridians.

The fresnelling based on a rotationally symmetrical target function generates a considerably reduced center thickness with respect to the prior art independently of the high cylindrical value of the eye lens 1, which has a rotationally symmetrical envelope 21 according to FIG. 3F, as it is shown in comparison of FIG. 3E and FIG. 3F.

In this configuration, it is provided that the stepped profile or the stepped contour course at the steep main meridian 13 is illustrated by the curve L3, whereas the contour course of the flat meridian 12 is illustrated by the curve L4. As is apparent from the representation in FIG. 3F, which represents the sagittal height S depending on the radius (r), the zones 18 to 20 are equally sized in the steep main meridian 13 and in the flat main meridian 12 in radial direction. Moreover, the step tips 15, 16 and 17 also have the two main meridians 12 and 13 and the same radial position. Moreover, it is also apparent from FIG. 3F how the step heights of the steps 19 to 20 differ in the two perpendicular main meridians 12 and 13. Therein, it is apparent that the step heights are larger in the steep main meridian 13 than in the flat main meridian 12. Thus, despite a rotationally symmetrical envelope 14 connecting the step tips 15 to 17 of the steps 18 to 20 both in the steep and in the flat main meridian 13 and 12, respectively, a toric refractive functionality is yet achieved by the different step heights in the main meridians. By these varying step heights, a toric refractive surface profile is virtually provided, on which the step heights of the steps 18 to 20 vary encircling in azimuthal direction. In this example, the steps are formed completely encircling the axis A and not equal to zero in any azimuthal position.

In contrast, the envelope 22 is shown in FIG. 3E.

In comparison between FIGS. 3E and 3F, the reduction of the thickness of the optical part is again apparent, wherein in this context the reduction of an embodiment of an eye lens according to the invention compared to the prior art is shown by d1 in the flat main meridian 12 and the reduction of the thickness of the optical part of an embodiment of an eye lens according to the invention compared to the prior art in the steep main meridian 13 is shown by d2. The reduction d1 is preferably between 0.15 and 0.3, in particular substantially 0.21. The reduction d2 is preferably between 0.3 and 0.5, preferably substantially 0.39.

Figures 3G, 3H:
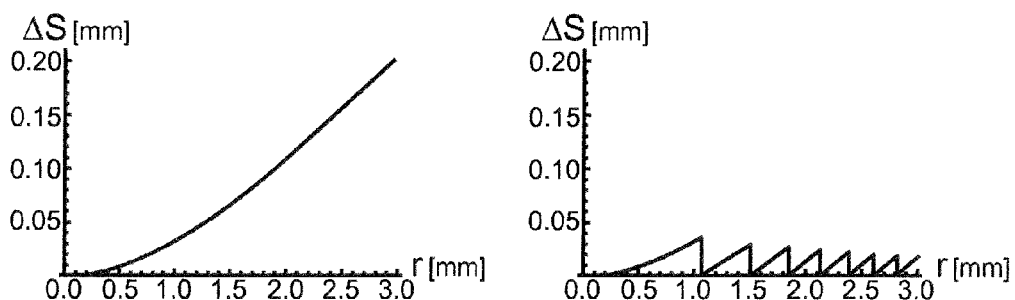
FIG. 3G is a diagram, in which the sagittal height difference between the two contour courses shown in FIG. 3E in the main meridians is illustrated.
FIG. 3H is a diagram, in which the sagittal height difference between the two perpendicular main meridians, as they are shown in the embodiment of an eye lens according to the invention in FIG. 3F, is represented.

In FIG. 3G, a diagram is shown, in which the sagittal height difference $\Delta S$ is shown depending on the radius (r) of the optical part 2 for the only toric intraocular lenses known from the prior art. In the diagram according to FIG. 3H, in contrast, the sagittal height difference $\Delta S$ is shown depending on the radius (r) for an embodiment of an eye lens 1 according to the invention. Here too, it is again apparent that this sagittal height difference $\Delta S$ decreases with increasing radius (r).

Figure 3I:
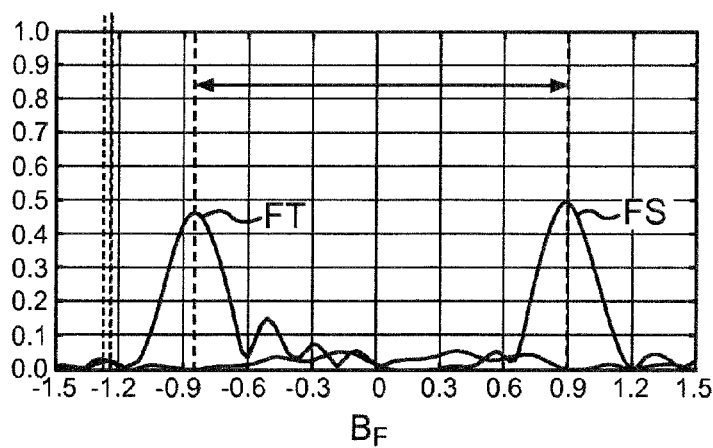
FIG. 3I is a diagram, in which the width of the tangential focus and the sagittal focus of the embodiment according to FIGS. 3A to 3D and 3F and 3H is shown.

In FIG. 3I, for the embodiment according to FIG. 3A ff., the focus width $B_F$ of the tangential focus FT and the sagittal focus FS is again shown, wherein here an astigmatism with about 8 diopters is characterized by the distance of the peaks of the foci.

Figure 3J:
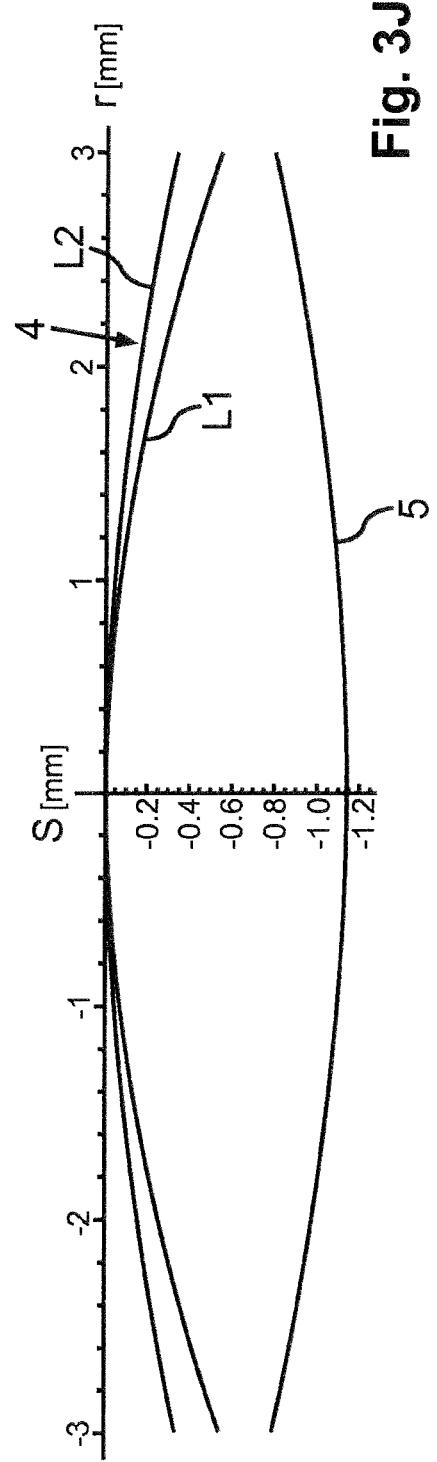
FIG. 3J is a diagram, in which the contour course of the rear side and the front side of an intraocular lens from the prior art is shown.

In FIG. 3J, a diagram is shown, in which the sagittal height is shown depending on the radius for the example known from the prior art of a purely toric intraocular lens, as it also already corresponds to the representation in FIG. 2L.

In FIG. 3K, a diagram is shown, in which the sagittal height is shown depending on the radius for the embodiment according to FIG. 3A ff. Here too, the substantial volume reduction of the optical part 2 is apparent. Similarly, the mirror-symmetric configuration to the plane E perpendicular to the axis A is here apparent. The contour course of the side 5 corresponds to the contour course of an envelope 14, as the step tips of the steps of the curve L3 and L4, which characterize the stepped rotationally symmetrical profiles in the steep main meridian 13 and in the flat main meridian 12.

In the embodiments explained heretofore of an eye lens according to the invention, the sides 4 and 5 are convexly curved.

Figure 3L:
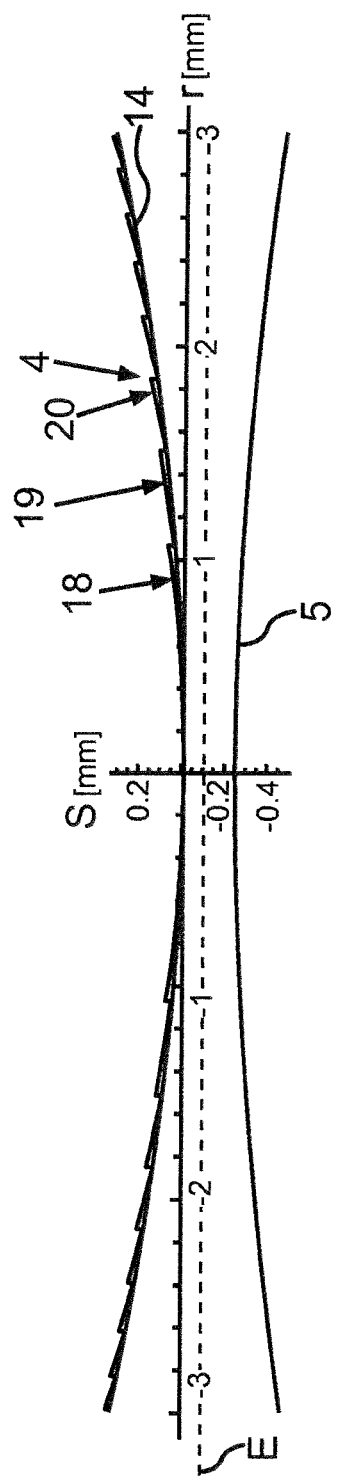
FIG. 3L is a diagram, in which the sagittal height is represented depending on the radius for a further embodiment of an eye lens according to the invention, in which both the front side and the rear side are concavely curved in contrast to the representation in FIG. 3K.

In FIG. 3L, a diagram is shown, in which the sagittal height is shown depending on the radius for a further embodiment of an eye lens according to the invention. In contrast to the implementations explained heretofore, here, it is provided that the side 4 and also the side 5 of the optical part 2 are each concavely curved. Here too, the configuration is such that the side 5 is mirror-symmetric to the envelope 14 in its contour course in mirroring on the plane E. The configuration shown in FIG. 3L is analogous to an embodiment, as it was explained in FIG. 2A ff. Moreover, an embodiment concave on both sides can also be provided, which corresponds to the configuration in FIG. 3K and thus is radially stepped in the perpendicular main meridians 12 and 13 and different step heights are formed in these main meridians for the steps.

In FIG. 4, a diagram is shown, in which a relation between a number of zones of an optical part 2, an area size of a cross-section of the optical part, and the step height is indicated. Herein, $S^*_H$ denotes the preferred limit of a minimum step height, CS* denotes a preferred limit for the course of the cross-sectional area and N* denotes the preferred limit for the zone number. The area between the limit lines is preferred for eye lenses of the invention. The cross-sectional area (sectional plane contains axis A) of the optical part is preferably between 3 and 4 mm², in particular between 3.2 and 3.8 mm².

In FIG. 5A, a table for a further embodiment of an eye lens is shown, in which for the exemplary number of 7 zones from left to right the parameters of the maximum zone radius, the radius of curvature r1 at the flat main meridian, the radius of curvature r2 at the steep main meridian, the curvature at the flat and at the steep main meridian, the curvature difference, the step heights "h-Fstep 0π" at the flat main meridian and the step heights "h-Fstep π/2" at the steep main meridian are shown. It is apparent that the step heights vary here. In contrast to the following example according to FIG. 7A ff., it is further that the cylindrical refractive power is 6 diopters and the radius of curvature RoC-Face2 is 10.7383 mm. The courses of the curves of the other parameters are identical in the curve shape, optionally deviate in the maximum values and/or minimum values.

Figure 5B:
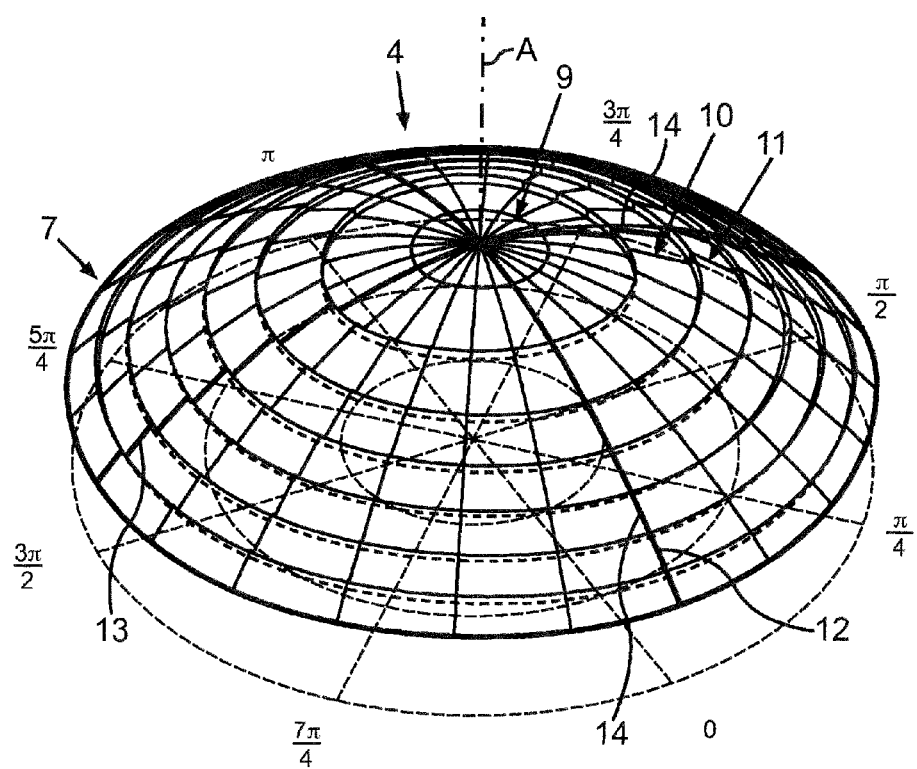
FIG. 5B is a three-dimensional representation of a surface topography of the front side according to the lens in the diagram in FIG. 5A.

In FIG. 5B, a three-dimensional surface topography of the embodiment is shown, in which the surface structure 8 and the surface profile 7 are exemplarily formed on a side 4 and commonly formed there. Here, analogously to the implementation in FIG. 2M, a stepping is not formed at the flat main meridian 12 and the contour course at the flat main meridian preferably corresponds to the envelope at the stepped steep main meridian and the contour course or the envelopes are rotationally symmetrical. Similarly, a mirroring of the rotationally symmetrical contour course on the plane E is in particular identical to the contour course of the side 5.

In FIG. 6A, a table comparable to FIG. 9A is shown for a further embodiment of the eye lens, in which for the exemplary number of 7 zones from left to right the parameters of the maximum zone radius, the radius of curvature r1 at the flat main meridian, the radius of curvature r2 at the steep main meridian, the curvature at the flat and at the steep main meridian, the curvature difference, the step heights "h-Fstep 0π" and "h-Fstep π/2" at the flat and the steep main meridian are shown. It is apparent that the step heights vary here. In contrast to the following example according to FIG. 9A ff., it is further that the cylindrical refractive power is 6 diopters and the radius of curvature RoC-Face2 is 19.329 mm. The courses of the curves of the other parameters are identical in the curve shape, optionally deviate in the maximum values and/or minimum values.

Figure 6B:
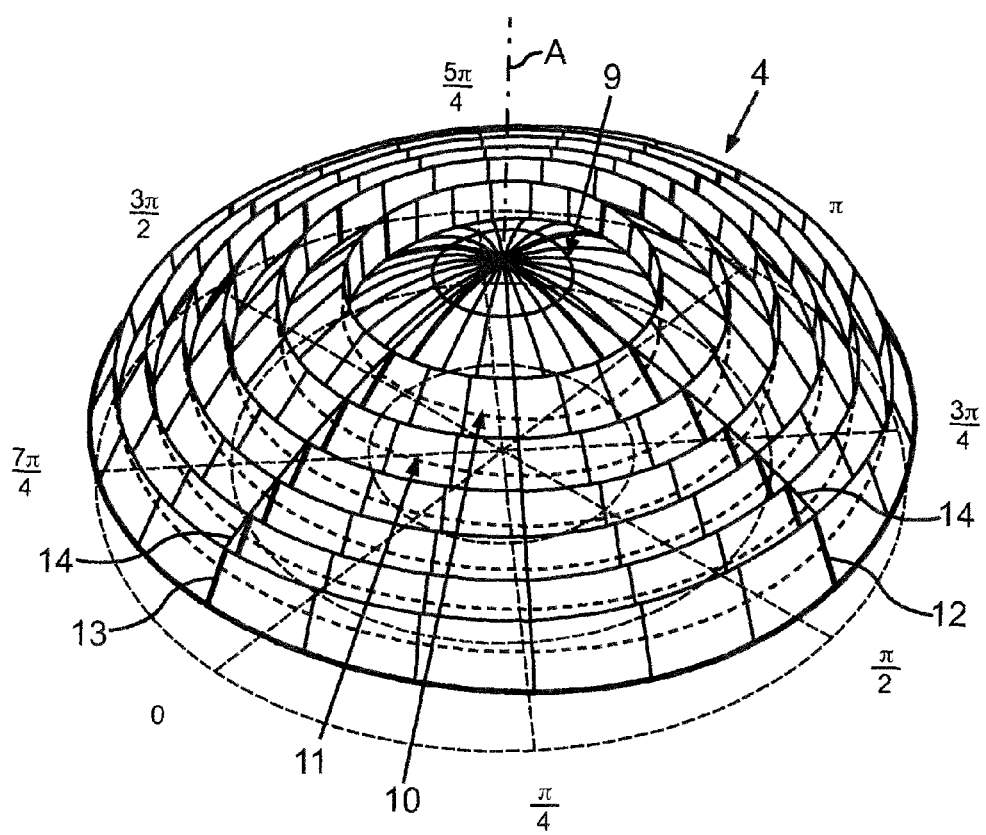
FIG. 6B is a three-dimensional representation of a surface topography of the front side according to the lens in the diagram in FIG. 6A.

In FIG. 6B, a three-dimensional surface topography of the embodiment is shown, in which the surface structure 8 and the surface profile 7 are exemplarily formed on a side 4 and commonly formed there. Here, analogous to the implementation in FIG. 3K, a stepping is formed at the flat main meridian 12 and at the steep main meridian 13 and the contour course of the envelope at the flat main meridian preferably corresponds to the envelope at the stepped steep main meridian and the contour course or the envelopes are preferably rotationally symmetrical. Similarly, mirroring of the rotationally symmetrical contour course on the plane E is in particular identical to the contour course of the side 5.

In FIGS. 7A to 7M, a further embodiment of an eye lens 1 is shown, in which a stepped surface structure 8 is formed, which is formed completely encircling. It is formed in addition to a toric refractive surface profile. Here, a configuration is realized, in which an envelope does not have rotational symmetry.

Exemplary parameter values for the spherical refractive power $F_{Sphäre}$, the cylindrical refractive power $F_{Cylinder}$, the center thickness CTVA, the radius of curvature RoC-Face2 (thus $r_S$), in particular the apex radius of curvature on the unstructured side and thus on the side of the optical part 2, on which the surface structure 8 and the surface profile 7 are not formed, the maximum radius $r_{max}$ of the optical part 2, the refractive index of the immersion medium (aqueous humor) and the refractive index of the material of the optical part 2, the number "Number of FZones" of the zones with steps and the step height $S_H$ ("Step Height").

Figure 7A:
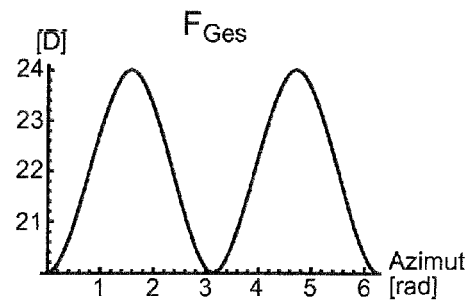
FIGS. 7A to 7J are a representation of diagrams, in which the overall refractive power, the spherical refractive power and the cylindrical refractive power of a further embodiment of an eye lens according to the invention as well as the course of the refractive power on a first side of the optical part and on a second side of the optical part are represented depending on the azimuth, and the overall refractive power, the radius, in particular the apex radius, the curvature, in particular the apex curvature, the conic constant and the sagittal height of the main meridians are represented depending on the normalized azimuthal angle.
Figure 7B:
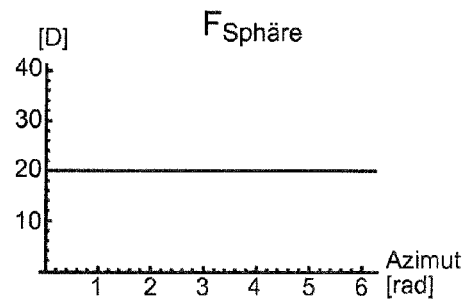
Figure 7C:
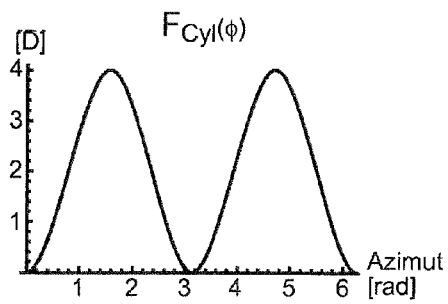

In FIG. 7A, the azimuthal course of the overall refractive power is shown. In FIGS. 7B and 7C, the azimuthal course of the spherical refractive power and the cylindrical refractive power is shown.

Figure 7D:
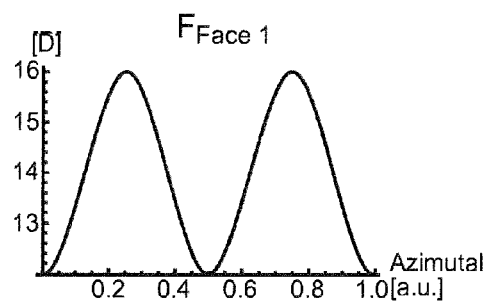
Figure 7E:
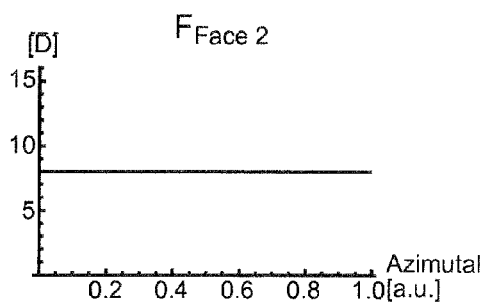

In FIG. 7D and FIG. 7E, the azimuthal course of the refractive power $F_{Face1}$ on the side of the optical part, on which the surface structure 8 and the surface profile 7 are formed (FIG. 7D) and the azimuthal course of the refractive power $F_{Face2}$ of the opposite side (FIG. 7E) are shown.

Figure 7F:
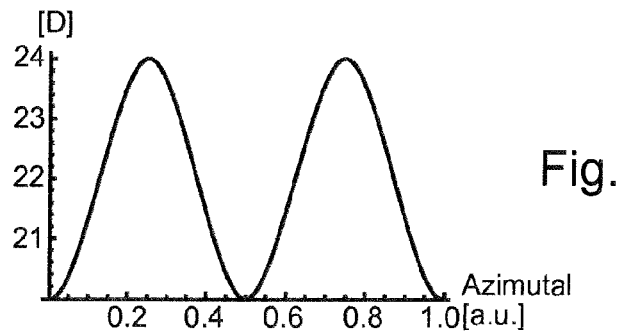
Figure 7G:
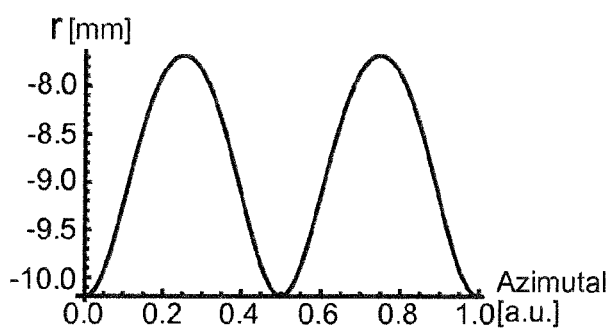
Figure 7H:
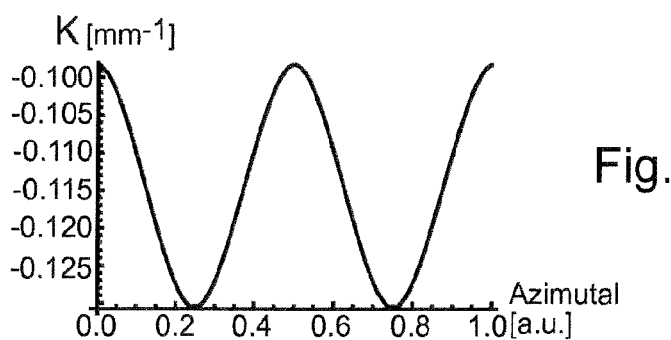
Figure 7I:
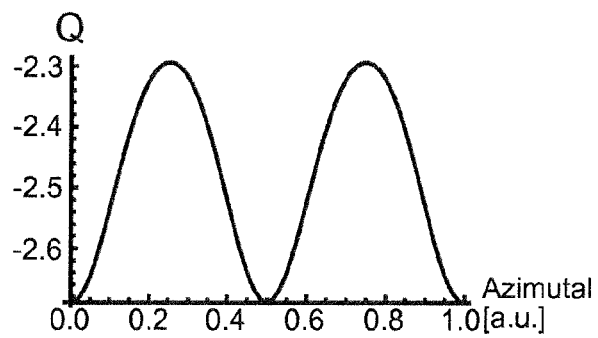
Figures 7J, 7K:
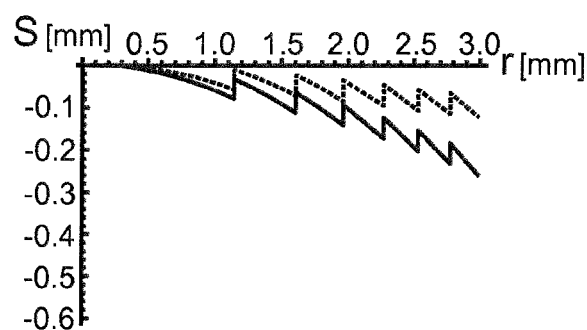
FIG. 7K is a table, in which values for the maximum radius, the radius at a flat main meridian and at a steep main meridian as well as the step height are represented for an exemplary number of zones of the eye lens according to FIGS. 7A to 7J.

In FIG. 7F, the course of the overall refractive power is shown depending on the normalized azimuthal angle. In FIG. 7G, the course of the apex radius is shown depending on the normalized azimuthal angle. In FIG. 7H, the course of the curvature K is shown depending on the normalized azimuthal angle. In FIG. 7I, the course of the conic constant (k) or Q is shown depending on the normalized azimuthal angle. In FIG. 7J, the course of the sagittal height S at the flat and the steep main meridian is shown depending on the normalized azimuthal angle.

In FIG. 7K, a table in shown, in which for the exemplary number of 7 zones from left to right the parameters of the maximum zone radius, the radius of curvature r1 at the flat main meridian, the radius of curvature r2 at the steep main meridian, and the step height of the steps are indicated. It is apparent that the step height here is constant.

Figure 7L:
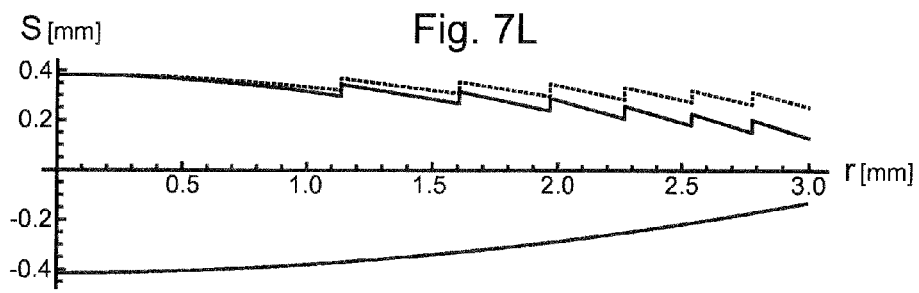
FIG. 7L is a diagram, in which the sagittal height of the front side with the contour courses in the flat and in the steep main meridian and the contour course of the rear side of the optical part of the eye lens according to FIGS. 5A to 5K are represented.

In FIG. 7L, a diagram is shown, in which the sagittal height is indicated depending on the radius (r) of the optical part 2, wherein here both the course of the rear side 5 and the courses of the flat and the steep main meridian, which are each stepped here, on the front side 4 are shown here.

Figure 7M:
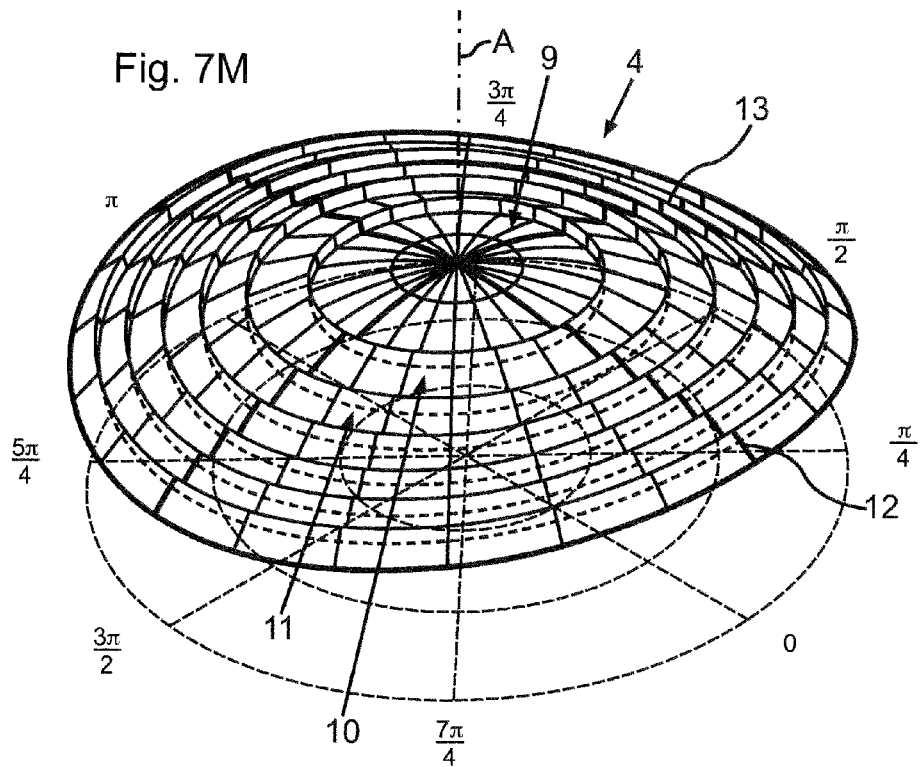
FIG. 7M is a three-dimensional representation of a surface topography of the front side of the lens according to the diagrams in FIGS. 7A and 7L.

In FIG. 7M, a three-dimensional surface topography of the embodiment is shown, in which the surface structure 8 and the surface profile 7 are exemplarily formed on one side 4 and commonly formed there.

Figures 8A, 8B:
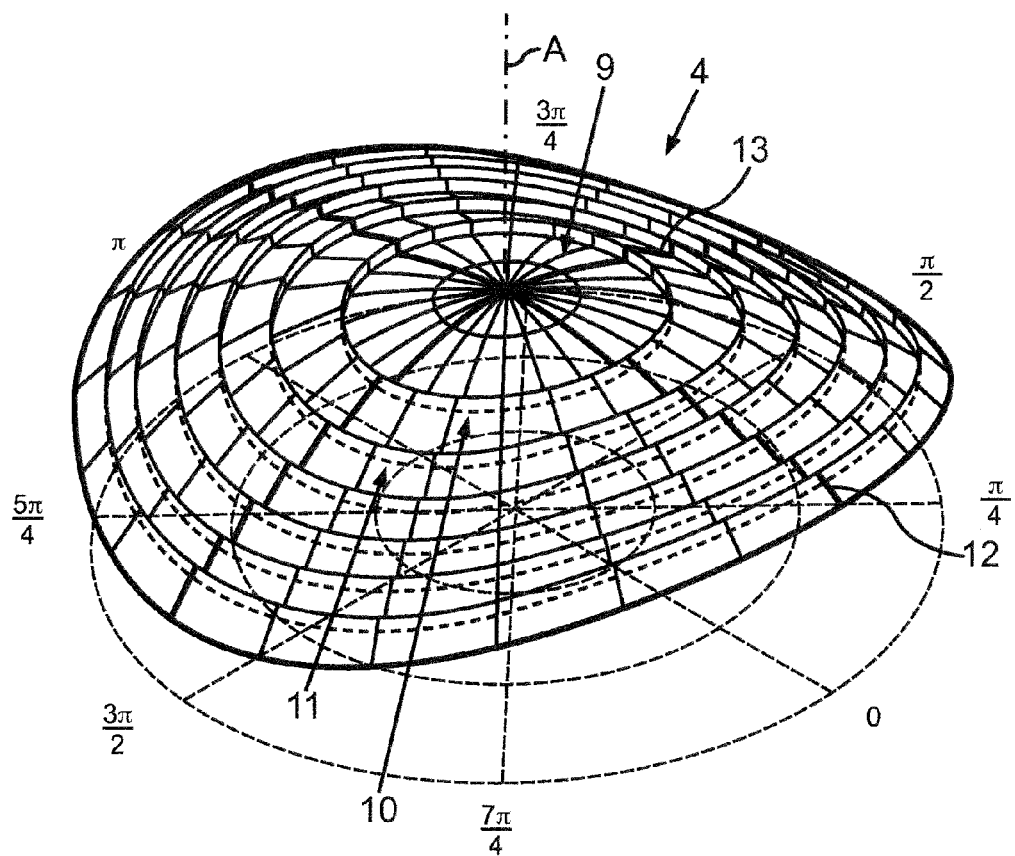
FIG. 8A is a table, in which values for the maximum radius, the radius at a flat main meridian and at a steep main meridian as well as the step height are represented for an exemplary number of zones of an eye lens, which has a cylindrical refractive power of 8 dpt and a radius of the rear side of 14.4027 mm compared to FIGS. 7A to 7M.
FIG. 8B is a three-dimensional representation of a surface topography of the front side according to the lens in the diagram in FIG. 8A.

In FIG. 8A, a table comparable to FIG. 7K is shown for a further embodiment of an eye lens, in which for the exemplary number of 7 zones from left to right the parameters of the maximum zone radius, the radius of curvature r1 at the flat main meridian, the radius of curvature r2 at the steep main meridian, and the step height of the steps are indicated. It is apparent that the step height here is constant. In contrast to the example according to FIG. 7A ff., it is further that the cylindrical refractive power is 8 diopters and the radius of curvature "RoC-Face2" is 14.4027 mm. The courses of the curves of the other parameters are identical in the curve shape, optionally deviate in the maximum values and/or the minimum values.

In FIG. 8B, a three-dimensional surface topography of the embodiment is shown, in which the surface structure 8 and the surface profile 7 are exemplarily formed on a side 4 and commonly formed there.

In FIG. 9, a table comparable to FIG. 5A is shown for a further embodiment of an eye lens, in which for the exemplary number of 7 zones from left to right the parameters of the maximum zone radius, the radius of curvature r1 at the flat main meridian, the radius of curvature r2 at the steep main meridian, and the step height of the steps are indicated. It is apparent that the step height $S_H$ varies here. In contrast to the example according to FIG. 5A ff, it is further that the cylindrical refractive power is 6 diopters. The courses of the curves of the other parameters are identical in the curve shape, optionally deviate in the maximum values and/or the minimum values.

Figure 10:
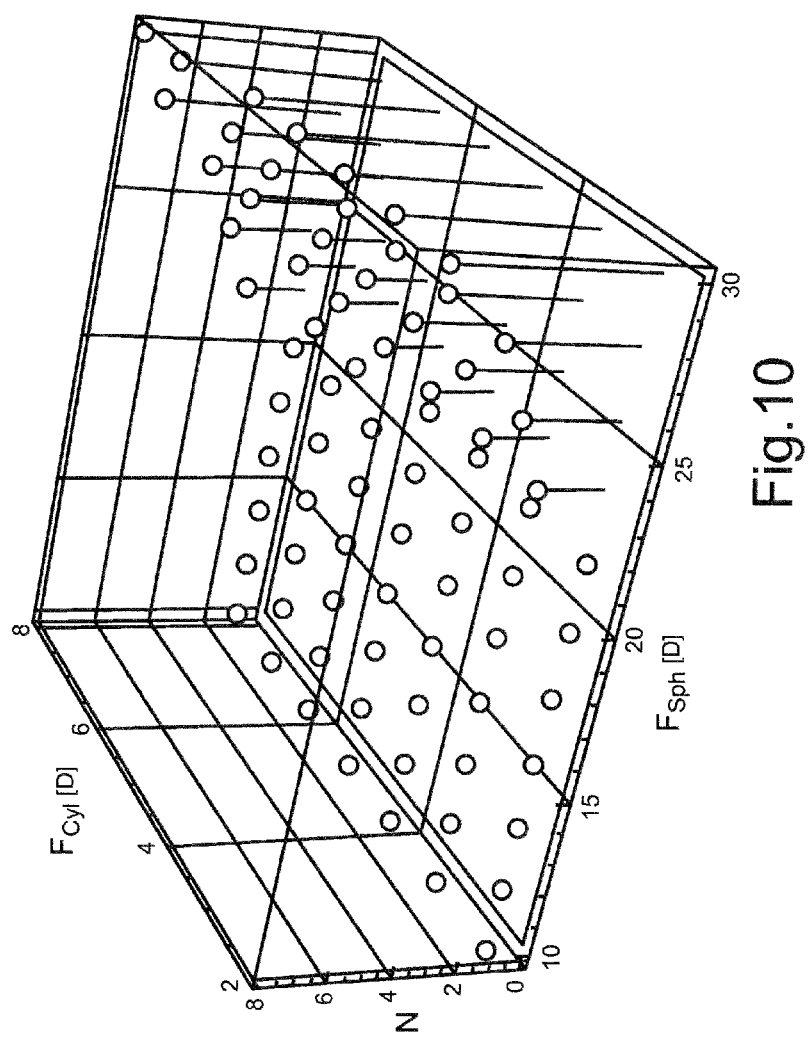
FIG. 10 is a diagram, in which a relation between a number of the annular optical zones generating a radially stepped surface structure, a cylindrical refractive power and a spherical refractive power is shown for embodiments of eye lenses according to the invention; and, FIG. 11 is a table, in which cross-sectional areas (A_cross) of the optical part for different spherical refractive powers $F_{sph}$, different cylindrical refractive powers $F_{cyl}$, different zone number N are indicated for embodiments of eye lenses according to the invention in two perpendicular cross-sectional planes.

In FIG. 10, a diagram is shown, in which a relation between a number N of annular optical zones generating a radially stepped surface structure, a cylindrical refractive power $F_{cyl}$, which is generated by the toric refractive surface profile and is contributed to the overall refractive power, and a spherical refractive power $F_{sph}$ is shown for embodiments of eye lenses according to the invention. The values are determined based on a refractive index value between 1.45 and 1.55, in particular 1.5, for the material of the optical part of the eye lens.

In FIG. 11, a table is shown, in which for different spherical refractive powers $F_{sph}$, different cylindrical refractive powers $F_{cyl}$, different zone number N, respective cross-sectional areas "A_cross" in $mm^2$ of the optical part are indicated for embodiments of eye lenses according to the invention in two perpendicular cross-sectional planes. Therein, it relates to the main meridians at zero and $\pi/2$. Here, the zone number N is indicated up to 8, but it can also be higher.

It is understood that the foregoing description is that of the preferred embodiments of the invention and that various changes and modifications may be made thereto without departing from the spirit and scope of the invention as defined in the appended claims.

What is claimed is:

1. An eye lens comprising:
   an optical part defining a main optical axis (A) and a radial direction;
   said optical part, viewed in the direction of said main optical axis (A), having a first optical side and a second optical side disposed opposite to said first optical side;
   a toric refractive surface profile formed on at least one of said first optical side and said second optical side;
   a surface structure in addition to said toric refractive surface profile;
   said surface structure being configured as a stepped surface structure stepped in said radial direction and formed on at least one of said first optical side and said second optical side;
   said stepped surface structure including a plurality of steps each having a step tip;
   said stepped surface structure having a radial contour course of an envelope connecting said step tips of said steps constituting said stepped surface structure formed on one of said first and said second optical sides; and,
   said radial contour course corresponding at least in sections to a second contour course of the other one of said first and second optical sides mirrored on a plane of symmetry (E) of the eye lens perpendicular on said main optical axis (A).

2. The eye lens of claim 1, wherein said toric refractive surface profile and said stepped surface structure are formed and superimposed on a common one of said first and said second optical sides.

3. The eye lens of claim 1, wherein said toric refractive surface profile is formed on said first optical side and said stepped surface structure is formed on said second optical side.

4. The eye lens of claim 1, wherein:
   said stepped surface structure includes a plurality of steps each having a step tip; and,
   said toric refractive surface profile has a flat main meridian defining a radial contour course identical to a second contour course of an envelope connecting said step tips of said steps constituting said stepped surface structure in a steep main meridian of said toric refractive surface profile.

5. The eye lens of claim 4, wherein a radial contour course of an envelope, which connects step tips of steps constituting the stepped surface structure in a flat main meridian of the toric refractive surface profile, is identical to a contour course of an envelope, which connects step tips of steps constituting the stepped surface structure in a steep main meridian of said toric refractive surface profile.

6. The eye lens of claim 1, wherein said radial contour course and said second contour course are rotationally symmetrical around said main optical axis (A).

7. The eye lens of claim 1, wherein:
   said stepped surface structure includes a plurality of steps each having a step tip; and,
   said step tips of said steps constituting the stepped surface structure in a flat main meridian of the toric refractive surface profile are formed radially at the same location as said step tips of said steps constituting the stepped surface structure in a steep main meridian of said toric refractive surface profile.

8. The eye lens of claim 1, wherein:
   said stepped surface structure includes a plurality of steps each having a step height; and,
   said step heights of steps constituting the stepped surface structure in a flat main meridian of the toric refractive surface profile are different than step heights of steps constituting the stepped surface structure in a steep main meridian of said toric refractive surface profile.

9. The eye lens of claim 1, wherein:
   said stepped surface structure includes a plurality of steps each having a step height; and,
   said step heights of steps constituting the stepped surface structure in a flat main meridian of the toric refractive surface profile are lower than step heights of steps constituting the stepped surface structure in a steep main meridian of said toric refractive surface profile.

10. The eye lens of claim 1, wherein:
    said stepped surface structure includes a plurality of steps each having a step height; and,
    said step heights of steps constituting the stepped surface structure are equal to zero only in a main meridian, in particular the flat main meridian, of the toric refractive surface profile.

11. The eye lens of claim 1, wherein said first optical side and said second optical side are each convexly formed.

12. The eye lens of claim 1, wherein said first optical side and said second optical side are each concavely formed.

13. The eye lens of claim 1, wherein a spherical refractive power portion of the overall refractive power of the eye lens is respectively equally distributed to said first optical side and said second optical side or a spherical refractive power portion of the overall refractive power of the eye lens is distributed at 25% to 35% to one of said first optical side and said second optical side and for the rest to the other one of said first optical side and said second optical side.

14. The eye lens of claim 1, wherein:
    said stepped surface structure includes a plurality of steps each having a step height; and,
    a difference value between a step height of a step at a steep main meridian and a step height of the step at a flat main meridian of said toric refractive surface profile decreases the more radially outwards the considered step is formed in the surface structure.

15. The eye lens of claim 1, wherein: the number of the annular zones constituting the stepped surface structure, at least partly encircling the principal axis (A), is between 5 and 14.

16. The eye lens of claim 1, wherein: the number of the annular zones constituting the stepped surface structure, at least partly encircling the principal axis (A), is between 7 and 14.

* * * * *